United States Patent [19]

Freyne et al.

[11] Patent Number: 5,037,829

[45] Date of Patent: Aug. 6, 1991

[54] (1H-AZOL-1-YLMETHYL) SUBSTITUTED QUINAZOLINE DERIVATIVES

[75] Inventors: Eddy J. E. Freyne, Rumst; Alfons H. M. Raeymaekers, Beerse, both of Belgium; Gerard C. Sanz, Garges les Gonesse; Marc G. Venet, Paris, both of France

[73] Assignee: Janssen Pharmaceutica N.V., Beerse, Belgium

[21] Appl. No.: 435,120

[22] Filed: Nov. 13, 1989

[30] Foreign Application Priority Data

Nov. 29, 1988 [GB] United Kingdom ............... 8827820

[51] Int. Cl.$^5$ .................. A61K 31/505; C07D 239/80
[52] U.S. Cl. ................................. 514/259; 544/284; 544/285; 544/286
[58] Field of Search ........................ 544/284; 514/259

[56] References Cited

U.S. PATENT DOCUMENTS

| 2,943,574 | 7/1990 | Raeymaekers et al. | 514/338 |
| 3,890,319 | 6/1975 | Danielewicz et al. | 544/284 |
| 4,532,250 | 7/1985 | Stout et al. | 544/284 |
| 4,859,684 | 8/1989 | Raeymaekers et al. | 514/314 |

FOREIGN PATENT DOCUMENTS 0260744 3/1988 European Pat. Off. .
0293978 12/1988 European Pat. Off. .

*Primary Examiner*—C. Warren Ivy
*Assistant Examiner*—James H. Turnipseed
*Attorney, Agent, or Firm*—Charles J. Metz

[57] ABSTRACT (1H-azol-1-ylmethyl)substituted quinazoline derivatives, compositions containing the same, and methods of treating mammals suffering from disorders which are characterized by an increased proliferation and/or abnormal differentiation of epithelial tissues.

20 Claims, No Drawings

(1H-AZOL-1-YLMETHYL) SUBSTITUTED QUINAZOLINE DERIVATIVES

BACKGROUND OF THE INVENTION

In the European Patent Application No. 260,744, published Mar. 3, 1988, which corresponds to U.S. Pat. No. 4,859,684, there are described (1H-azol-1-ylmethyl) substituted benzimidazole derivatives which compounds are useful as androgenic hormone biosynthesis inhibitors. The compounds of the present invention differ from the cited art compounds by the fact that they contain a quinazoline moiety in place of an benzimidazole moiety and by their favourable pharmaceutical properties. In particular the compounds of the invention suppress the plasma elimination of retinoic acids. Further it was shown that some compounds inhibit the action of the enzyme complex a romatase which catalyses the formation of estrogens from androgenic steroids in mammals.

DESCRIPTION OF THE INVENTION

The present invention is concerned with novel compounds of formula

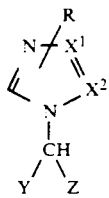
(I)

the pharmaceutical by acceptable acid addition salts thereof and the stereochemically isomeric forms thereof,
wherein
—$X^1$=$X^2$— is a bivalent radical having the formula

—CH=CH— (x),

—CH=N— (y), or

—N=CH— (z);

R is hydrogen or $C_{1-6}$alkyl;
Y is hydrogen; $C_{1-10}$alkyl; $C_{3-7}$cycloalkyl; $Ar^1$; $Ar^2$-$C_{1-6}$alkyl; $C_{2-6}$alkenyl or $C_{2-6}$alkynyl;
Z is a radical of formula

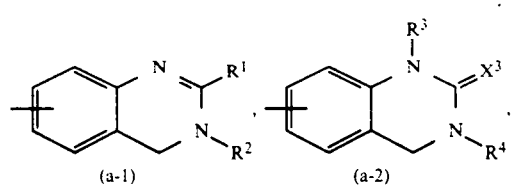

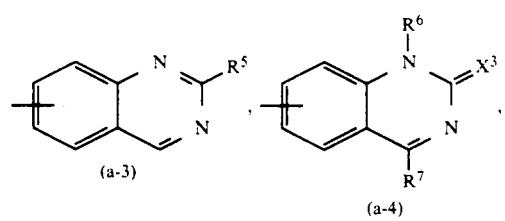

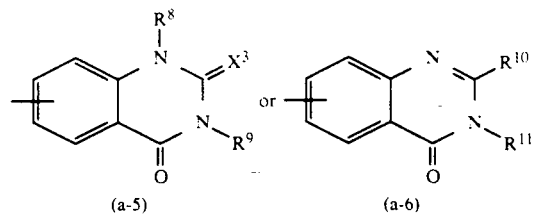

wherein
$R^1$, $R^5$ and $R^{10}$ each independently are hydrogen, halo, $C_{1-6}$alkyl, trifluoromethyl, $C_{1-6}$alkyloxy, $Ar^2$, $Ar^2$-$C_{1-6}$alkyl, amino, or mono- or di($C_{1-6}$alkyl)amino;
$R^2$, $R^4$ and $R^9$ each independently are hydrogen, $C_{1-6}$alkyl, $Ar^2$ or $Ar^2$-$C_{1-6}$alkyl;
$R^3$, $R^6$ and $R^8$ each independently are hydrogen, $C_{1-6}$alkyl or $Ar^2$-$C_{1-6}$alkyl;
$R^7$ is hydrogen or $C_{1-6}$alkyl;
$R^{11}$ is hydrogen, $C_{1-6}$alkyl, $Ar^2$-$C_{1-6}$alkyl, amino or mono($C_{1-6}$alkyl)amino;
$X^3$ is O or S; and
$Ar^1$ is phenyl, substituted phenyl, naphthalenyl, pyridinyl, imidazolyl, triazolyl, thienyl, furanyl or thiazolyl and $Ar^2$ is phenyl or substituted phenyl; said substituted phenyl in $Ar^1$ or $Ar^2$ being phenyl substituted with 1, 2 or 3 substituents each independently selected from halo, hydroxy, trifluoromethyl, $C_{1-6}$alkyl, $C_{1-6}$alkyloxy, cyano, amino, mono- and di($C_{1-6}$alkyl)amino, nitro, carboxyl, formyl and $C_{1-6}$alkyloxycarbonyl.

As used in the foregoing definitions the term halo is generic to fluoro, chloro, bromo and iodo; the term "$C_{1-6}$alkyl" is meant to include straight chained and branched saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "$C_{1-10}$alkyl" is meant to include the higher homologs of "$C_{1-6}$alkyl" containing 1-10 carbon atoms; the term "$C_{3-7}$cycloalkyl" is generic to cyclopropyl, cyclobutyl, cyclopentyl, cyclohexyl and cycloheptyl; "$C_{2-6}$alkenyl" defines straight chained and branched hydrocarbon radicals containing one double bond having from 2 to 6 carbon atoms such as, for example, ethenyl, 2-propenyl, 3-butenyl, 2-butenyl, 2-pentenyl, 3-pentenyl, 3-methyl-2-butenyl and the like; "$C_{2-6}$alkynyl" defines straight chained and branched hydrocarbon radicals containing one triple bond and having from 2 to 6 carbon atoms such as, for example, 2-propynyl, 2-butynyl, 3-butynyl, 2-pentynyl, 3-pentynyl, 4-pentynyl and the like.

It is to be understood that the

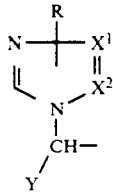

moiety hereinafter referred as the 1H-azol-1-ylmethyl moiety may be substituted on either the 5, 6, 7 or 8 position of the bicyclic ring system, in particular on the 6 and 7 position, with the 6 position being preferred.

Further it should be noted that the compounds of formula (I) wherein Z is a radical of formula (a-1) are denoted as compounds of formula (I-a-1); compounds of formula (I) wherein Z is a radical of formula (a-2) are denoted as compounds of formula (I-a-2); compounds of formula (I) wherein Z is a radical of formula (a-3) are denoted as compounds of formula (I-a-3); compounds of formula (I) wherein Z is a radical of formula (a-4) are denoted as compounds of formula (I-a-4); compounds of formula (I) wherein Z is a radical of formula (a-5) are denoted as compounds of formula (I-a-5) and compounds of formula (I) wherein Z is a radical of formula (a-6) are denoted as compounds of formula (I-a-6).

The acid addition salts as mentioned hereinabove are meant to comprise the therapeutically active non-toxic acid addition salt forms which the compounds of formula (I) are able to form. The latter can conveniently be obtained by treating the base form with appropriate acids such as, for example, inorganic acids, such as hydrohalic acid, e.g. hydrochloric, hydrobromic and the like, and sulfuric acid, nitric acid, phosphoric acid and the like; or organic acids such as, for example, acetic, hydroxyacetic, propanoic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The term acid addition salt also comprises the hydrates and solvent addition forms which the compounds of formula (I) are able to form. Examples of such forms are e.g. hydrates, alcoholates and the like.

From formula (I) it is evident that the compounds of this invention may have several asymmetric carbon atoms in their structure. Pure isomeric forms of the compounds of formula (I) can be separated from the mixture by conventional separation methods.

Preferably, if a specific stereoisomer is desired, said compound will be synthesized by stereoselective methods of preparation. These methods will advantageously employ enantiomerically pure starting materials.

Further it is evident that the compounds of formula (I) may also contain in their structure a tautomeric system and consequently these compounds can be present in each of their tautomeric forms.

Particular compounds of the present invention are those compounds of formula (I) wherein R is hydrogen; and/or Y is hydrogen, $C_{1-6}$alkyl, $C_{3-7}$cycloalkyl, phenyl, substituted phenyl, pyridinyl, imidazolyl or thienyl; and/or Z is a radical of formula (a-1), (a-2), (a-3), (a-4), (a-5), or (a-6) wherein $R^1$ is hydrogen, $C_{1-4}$alkyl, trifluoromethyl or phenyl, $R^2$ is hydrogen, $C_{1-4}$alkyl, phenyl or phenyl$C_{1-4}$alkyl, $R^3$ is hydrogen or $C_{1-4}$alkyl substituted with phenyl, $R^4$, $R^5$, $R^6$, $R^7$ and $R^8$ are hydrogen or $C_{1-4}$alkyl, $R^9$ is hydrogen, $C_{1-4}$alkyl or phenyl$C_{1-4}$alkyl, $R^{10}$ is hydrogen, amino or mono or di($C_{1-4}$alkyl)amino, and $R^{11}$ is hydrogen.

More particular compounds are those particular compounds wherein $-X^1=X^2-$ is a radical of formula (x) or (y); and/or R is hydrogen; and/or Y is hydrogen, $C_{1-4}$alkyl, cyclopropyl, cyclohexyl, pyridinyl or phenyl optionally substituted with one or two substituents selected from halo, $C_{1-4}$alkyl, $C_{1-4}$alkyloxy and trifluoromethyl.

Among the compounds of the aforementioned subgroups special emphasis is put on compounds of formula (I) wherein Z is a radical of formula (a-2) wherein $R^3$ is hydrogen, $R^4$ is hydrogen or $C_{1-4}$alkyl and Y is hydrogen, $C_{1-4}$alkyl, pyridinyl or phenyl optionally substituted with one or two halo atoms; and compounds of formula (I) wherein Z is a radical of formula (a-3) wherein $R^5$ is $C_{1-4}$alkyl and Y is phenyl or halophenyl; and compounds of formula (I) wherein Z is a radical of formula (a-5) wherein $R^8$ is hydrogen, $R^9$ is hydrogen, $C_{1-4}$alkyl or phenyl$C_{1-4}$alkyl and Y is hydrogen, phenyl or halophenyl; and compounds of formula (I) wherein Z is a radical of formula (a-6) wherein $R^{10}$ is hydrogen or amino, $R^{11}$ is hydrogen and Y is hydrogen, phenyl or halophenyl.

Preferred compounds of formula (I) wherein Z is a radical of formula (a-2) are those compounds wherein $-X^1=X^2-$ is a radical having the formula (x) or (y); R is hydrogen; $R^3$ is hydrogen; $R^4$ is hydrogen; and Y is phenyl, halophenyl or propyl.

Most preferred compounds of formula (I) wherein Z is a radical of formula (a-2) are selected from 3,4-dihydro-6-[(1H-imidazol-1-yl)phenylmethyl]-2-(1H)-quinazolinone, the pharmaceutically acceptable acid addition salts and possible stereochemically isomeric forms thereof.

Preferred compounds of formula (I) wherein Z is a radical of formula (a-5) are those compounds wherein $-X^1=X^2-$ is a radical having the formula (x) or (y); R is hydrogen; $R^8$ is hydrogen; $R^9$ is hydrogen, methyl or $C_{1-4}$alkylphenyl; and Y is phenyl or halophenyl.

Most preferred compounds of formula (I) wherein Z is a radical of formula (a-5) are selected from 6-[(1H-imidazol-1-yl)phenylmethyl]-3-methyl-2,4(1H,3H)-quinazolinedione, the pharmaceutically acceptable acid addition salts and possible stereochemically isomeric forms thereof.

Preferred compounds of formula (I) wherein Z is a radical of formula (a-6) are those compounds wherein $-X^1=X^2-$ is a radical having the formula (x) or (y); R is hydrogen; $R^{10}$ is hydrogen; $R^{11}$ is hydrogen; and Y is phenyl or halophenyl.

Most preferred compounds of formula (I) wherein Z is a radical of formula (a-5) are selected from 6-[(1H-imidazol-1-yl)phenylmethyl]-4(3H))-quinazolinone, the pharmaceutically acceptable acid addition salts and possible stereochemically isomeric forms thereof.

The compounds of formula (I) can be prepared by N-alkylating an azole of formula (II) or an alkali metal salt thereof with a quinazoline derivative of formula (III).

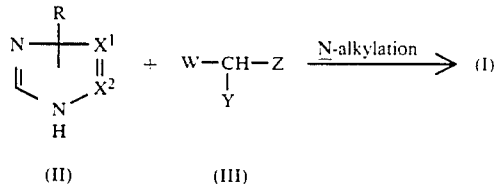

In formula (III) W represents an appropriate reactive leaving group such as, for example, halo, e.g., fluoro, chloro, bromo, iodo or a sulfonyloxy group, e.g. 4-methylbenzenesulfonyloxy, benzenesulfonyloxy, 2-naphthalenesulfonyloxy, methanesulfonyloxy, trifluoromethanesulfonyloxy and the like reactive leaving groups.

The above described N-alkylation is conveniently carried out by stirring the reactants in the presence of a suitable solvent such as, for example, an aromatic hydrocarbon, e.g. benzene, methylbenzene, dimethylbenzene, and the like; an ester, e.g. ethyl acetate, γ-butyrolacetone and the like; a ketone, e.g. 2-propanone, 4-methyl-2-pentanone and the like; an ether, e.g. 1,4-dioxane, 1,1'-oxybisethane, tetrahydrofuran and the like; a polar aprotic solvent, e.g. N,N-dimethylformamide, N,N-dimethylacetamide, dimethylsulfoxide, 1-methyl-2-pyrrolidinone, acetonitrile, hexamethylphosphor triamide, 1,3-dimethyl-3,4,5,6-tetrahydro-2(1H)-pyrimidinone, 1,3-dimethyl-2-imidazolidinone, benzonitrile and the like; or a mixture of such solvents. Somewhat elevated temperatures may be appropriate to enhance the rate of the reaction and in some cases the reaction may even be carried out at the reflux temperature of the reaction mixture. The addition of an appropriate base such as, for example, an alkali or an earth alkaline metal carbonate, hydrogen carbonate, hydroxide, amide or hydride, e.g. sodium hydroxide, potassium hydroxide, potassium carbonate, sodium hydride and the like or an organic base, such as, for example, N,N-dimethyl-4-pyridinamine, pyridine, N,N-diethylethanamine or N-(1-methylethyl)-2-propanamine may be employed to pick up the acid which is liberated during the course of the reaction. In some instances it may be advantageous to use an excess of the azole (II) or to convert the azole first into a suitable salt form thereof such as, for example, an alkali or earth alkaline metal salt, by reacting (II) with an appropriate base as defined hereinabove and subsequently using said salt form in the reaction with the alkylating reagent of formula (III). Additionally, it may be advantageous to conduct said N-alkylation reaction under an inert atmosphere such as, for example, oxygen-free argon or nitrogen gas. Said alkylation may also be carried out by applying art-known conditions of phase transfer catalysis reactions.

Compounds of formula (I) wherein —X¹=X²— is a bivalent radical of formula (x), said compounds being represented by formula (I-x), may also be prepared by reacting a quinazoline of formula (III) with a 1-protected imidazole of formula (II-x) following the N-alkylation procedures described hereinabove for the preparation of compounds of formula (I) starting from (II) and (III).

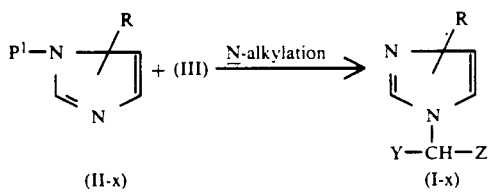

(II-x)                (I-x)

In (II-x) P¹ represents a protective group such as, for example, $C_{1-6}$alkylcarbonyl, $C_{1-6}$alkyloxycarbonyl, arylcarbonyl or a tri($C_{1-6}$alkyl)silyl group. In some instances the reaction of (II-x) with (III) first yields a 1-protected imidazolium salt of formula (IV) which may in situ, or if desired, after isolating and further purifying it, be deprotected by stirring it in an aqueous basic solution or acidic solution.

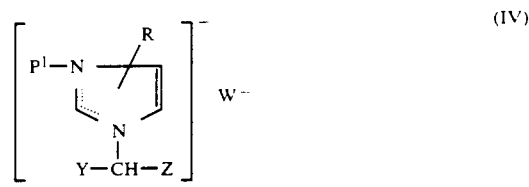

In (IV) $W^-$ is an anion arising from an acid such as, for example, hydrochloric acid, hydrobromic acid, methanesulfonic acid, 4-methylbenzenesulfonic acid and the like acids.

Compounds of formula (I) wherein —X¹=X²— is a bivalent radical of formula (y), said compounds being represented by formula (I-y), can also be prepared by endo-N-alkylation of a triazolamine of formula (II-y) with a quinazoline of formula (III) and subsequent deamination of the thus prepared triazolium salt, wherein $W^-$ is an anion as defined hereinabove.

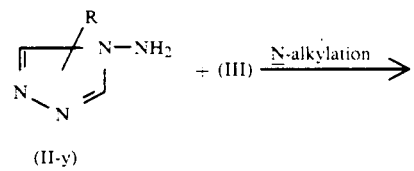

(II-y)

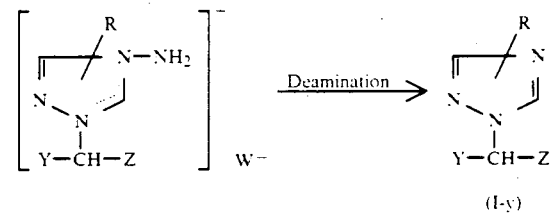

(I-y)

The endo-N-alkylation reaction of (II-y) with (III) is carried out according to similar procedures as described hereinabove for the preparation of a compound of formula (I) starting from (III) and (II). Said deamination reaction is conveniently conducted by reaction with an acidic nitrite solution in the presence of an appropriate reductant, or by reaction with an alkylnitrite such as, for example, 1,1-dimethylethylnitrite or isoamylnitrite and the like. Preferably, said deamination reaction is conducted with an aqueous solution of nitrous acid or of a nitrite salt in a suitable acid in the presence of a reducing agent such as, for example, hypophosphorous acid, formic acid, at a lower temperature.

The quinazolines of formula (I) may also be prepared by reacting an intermediate of formula (V) with a reagent of formula (VI) such as, for example, 1,1'-carbonylbis[1H-imidazole], 1,1'-carbonylbis[1H-triazole] and the like.

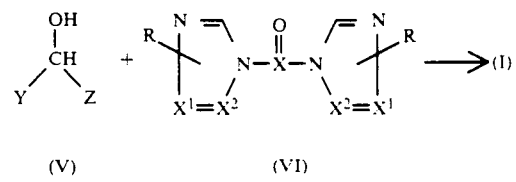

(V)                (VI)

In (VI) X represents C or S.

Said reaction may conveniently be conducted in a suitable solvent such as, for example, an ether, e.g. 1,4- dioxane, tetrahydrofuran; a halogenated hydrocarbon, e.g. di- or trichloromethane; a hydrocarbon, e.g. benzene, methylbenzene; a ketone, e.g. 2-propanone, 4-methyl-2-pentanone; N,N-dimethylformamide, N,N-dimethylacetamide, or a mixture of such solvents. In order to enhance the reaction rate, it may be advantageous to heat the reaction mixture.

The compounds of formula (I) may also be prepared by reacting a ketone or aldehyde of formula (VII) with an azole (II) in the presence of formic acid or formamides as reducing agents.

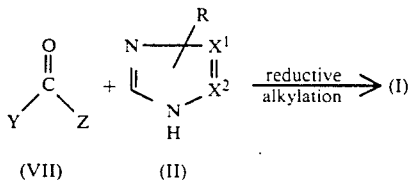

In all of the foregoing and following preparations, the reaction products may be isolated from the reaction mixture and, if necessary, further purified according to methodologies generally known in the art such as, for example, extraction, distillation, crystallization, trituration and chromatography.

Some compounds of formula (I) can alternatively be prepared according to similar procedures as are described in the literature for the preparation of quinazolines and their analogs by cyclizing an appropriate starting compound.

For example, compounds of formula (I-a-1) may be prepared by reacting an intermediate of formula (VIII) with a carboxylic acid of formula (IX) or a functional derivative thereof.

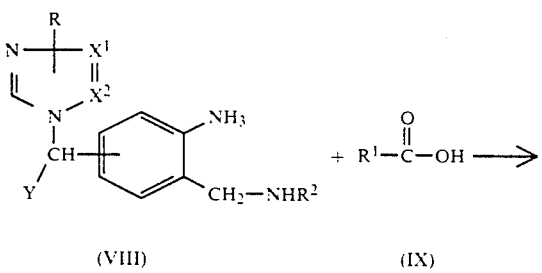

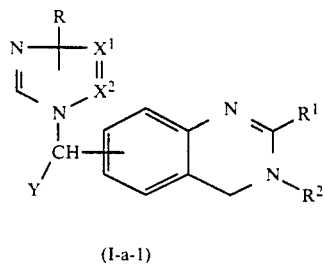

Said functional derivative of (IX) is meant to comprise the halide, anhydride, amide and ester form of (IX), including the ortho and imino ester form thereof. The cyclization of (VIII) and (IX) is preferably carried out by mixing the reactants, optionally in a reaction inert solvent such as, for example, water; a $C_{1-6}$alkanol, e.g. methanol, ethanol, 1-butanol and the like; an ester, e.g. ethyl acetate; a halogenated hydrocarbon, e.g. trichloromethane, dichloromethane and the like; or a mixture of such solvents, preferably in the presence of a mineral acid such as, for example, hydrochloric acid, sulfuric acid and the like, or a carboxylic acid such as, for example, formic acid, acetic acid and the like, or a sulfonic acid such as, for example, methanesulfonic, benzenesulfonic, 4-methylbenzenesulfonic acid and the like or in the presence of an appropriate dehydrating agent such as for example, polyphosphoric acid, phosphorous pentoxide and the like. Somewhat elevated temperatures may be appropriate to enhance the rate of the reaction and in some cases the reaction may even be carried out at the reflux temperature of the reaction mixture. In the instance where (IX) is an acid or the corresponding alkyl ester thereof, the cyclization reaction of (VIII) and (IX) may be conducted in the presence of a suitable dehydrating agent such as, for example, polyphosphoric acid, phosphorous pentoxide, polyphosphate ester and the like. In a preferred method of conducting the above cyclization reaction there is used the imino ester form of (IX) in an acidic medium such as, for example, acetic acid, or a $C_{1-6}$alkanol, whereto an appropriate acid, e.g. hydrochloric acid has been added in case the imino ester is not in the form of an acid addition salt.

The compounds of formula (I-a-1) may also be obtained by cyclizing an intermediate of formula (X).

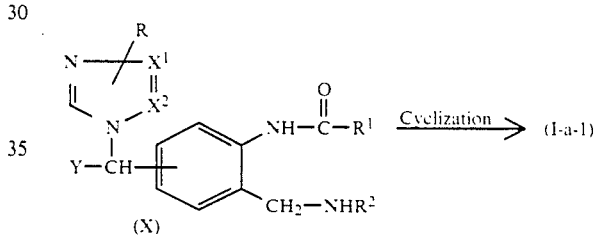

Said cyclization reaction may conveniently be conducted by heating intermediate (X) in an appropriate reaction-inert solvent such as, for example, an aromatic hydrocarbon, e.g., benzene, methylbenzene, dimethylbenzene and the like, a halogenated hydrocarbon, e.g., trichloromethane, tetrachloromethane and the like, an alkanol, e.g., ethanol, propanol, butanol and the like, a ketone, e.g., 2-propanone, 4-methyl-2-pentanone and the like, a dipolar aprotic solvent, e.g., N,N-dimethylformamide, N,N-dimethylacetamide, acetonitrile, pyridine and the like, or a mixture of such solvents, and optionally removing the water which is liberated during the course of the cyclization reaction by azeotropical distillation. It may be appropriate to add to the reaction mixture an acid catalyst such as, for example, a mineral acid, e.g., hydrochloric, sulfuric and the like acids, a carboxylic acid, e.g., acetic acid, trifluoroacetic acid and the like, a sulfonic acid, e.g., methanesulfonic, benzenesulfonic or 4-methylbenzenesulfonic acid and the like.

The compounds of formula (I-a-2) may be obtained by reacting an intermediate of formula (VIII-a) with a reagent of formula $L-C(=X^3)-L$ (XI) wherein L represents a reactive leaving group and $X^3$ is oxygen or sulfur.

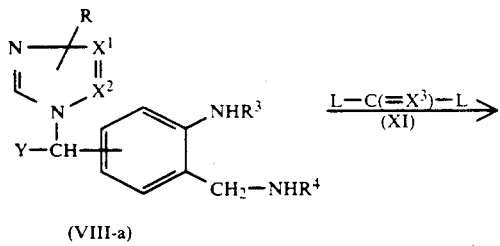

(VIII-a)

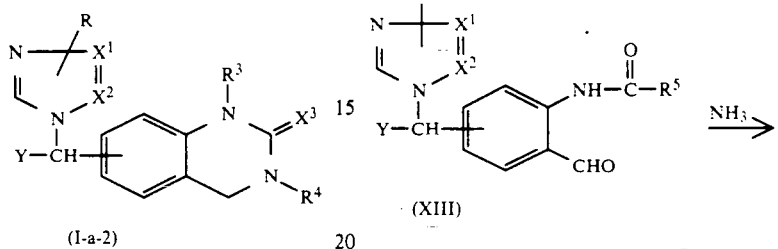

(I-a-2)

As examples of reagents of formula L—C(=X³)—L (XI) there may be mentioned urea, thiourea, 1,1'-sulfinylbis[1H-imidazole], 1,1'-carbonylbis[1H-imidazole], alkylcarbonohalidates, e.g., ethyl carbonochloridate and the like, dialkylcarbonates, carbonoic dichloride, carbonothioic dichloride, trichloromethyl chloroformate, carbon disulfide, trifluoromethyl carbonohalidate and the like reagents. Said reaction may be carried out by stirring the reactants, optionally in a reaction-inert solvent such as, for example, an ether, e.g. 1,1'-oxybisethane, tetrahydrofuran; a halogenated hydrocarbon, e.g. dichloromethane, trichloromethane; a hydrocarbon, e.g. benzene, methylbenzene; an alcohol, e.g. methanol, ethanol; a ketone, e.g. 2-propanone, 4-methyl-2-pentanone; a polar aprotic solvent, e.g. N,N-dimethylformamide, N,N-dimethylacetamide, acetonitrile, or a mixture of such solvents. In some instances it may be appropriate to add to the reaction mixture a base such as, for example, an alkali or earth alkaline metal carbonate, hydrogen carbonate, hydroxide or oxide, for example, sodium carbonate, sodium hydrogen carbonate, potassium carbonate, sodium hydroxide, potassium hydroxide and the like, or an organic base, for example, N,N-diethylethanamine, N-(1-methylethyl)-2-propanamine and the like. In order to enhance the reaction rate, it may be advantageous to heat the reaction mixture.

Alternatively, the compounds of formula (I-a-2) can also be prepared by reducing and condensing an intermediate of formula (XII) in a reaction-inert solvent.

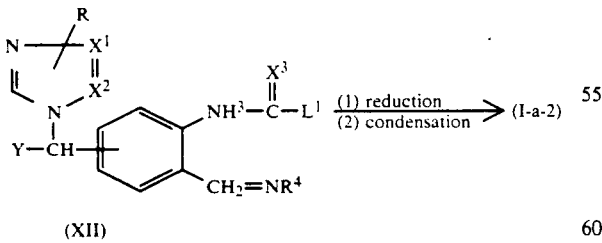

(XII)

In formula (XII) L¹ represents a reactive leaving group such as, for example, amino or alkyloxy, e.g., methoxy, ethoxy and the like. Reaction-inert solvents are, for example, alkanols, e.g., methanol, ethanol, butanol and the like, aromatic hydrocarbons, e.g., benzene, methylbenzene and the like, halogenated hydrocarbons, e.g. trichloromethane, tetrachloromethane and the like.

Said reduction can conveniently be carried out by treating (XII) with a reducing agent such as, for example, an alkali metal borohydride, e.g. lithium, potassium or, preferably, sodium borohydride, sodium cyanoborohydride and the like reducing agents.

The compounds of formula (I-a-3), may be prepared by reacting an intermediate of formula (XIII) with ammonia.

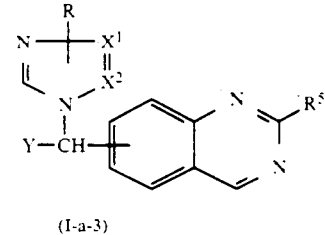

(XIII)

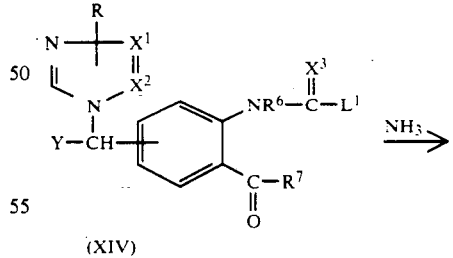

(I-a-3)

Said reaction may conveniently be conducted by stirring the reactants in an appropriate solvent such as, for example, and alkanol, e.g., methanol, ethanol and the like, an ether, e.g., 1,1'-oxybisethane, tetrahydrofuran, 1,4-dioxane and the like, an aromatic hydrocarbon, e.g., benzene, methylbenzene, dimethylbenzene and the like, a halogenated hydrocarbon, e.g. trichloromethane, tetrachloromethane and the like solvents.

In a similar manner, the compounds of formula (I-a-4), may be obtained from an intermediate of formula (XIV) wherein L¹ represents a leaving group as defined hereinabove, by reaction with ammonia, following the procedures described hereinabove for the preparation of the compounds of formula (I-a-3) from the intermediates (XIII).

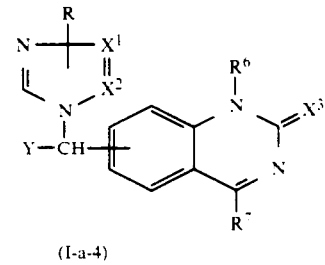

(XIV)

(I-a-4)

Compounds of formula (I-a-4) wherein $R^7$ is $C_{1-6}$alkyl may be prepared by cyclizing an intermediate of formula (XV) in the presence of a suitable dehydrating agent such as, for example, polyphosphoric acid, phosphorous pentoxide and the like. In (XV) and (I-a-4) $R^{7-a}$ represents $C_{1-6}$alkyl.

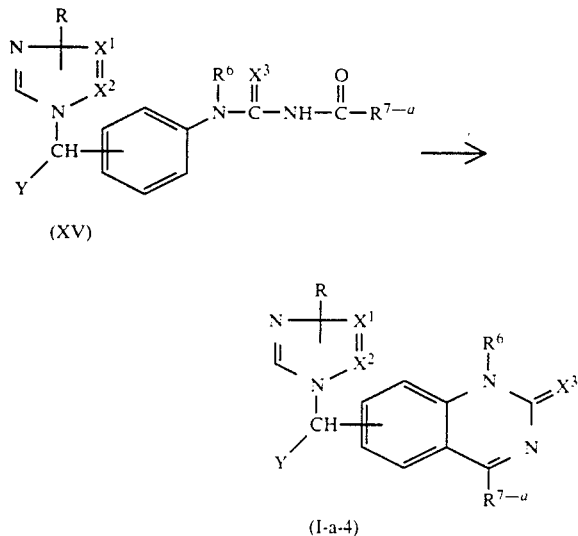

The compounds of formula (I-a-5), may be prepared by condensing an intermediate (XVI) with a reagent $L-C(=X^3)-L$ (XI), as defined hereinabove.

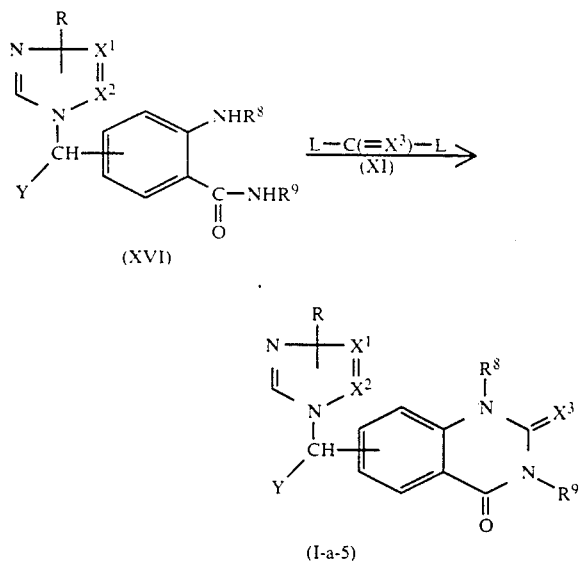

Said cyclization reaction may conveniently be conducted following the procedures described hereinabove for the preparation of the compounds of formula (I-a-2) from the intermediates (VIII-a) and the reagent $L-C(=X^3)-L$ (XI).

The compounds of formula (I-a-6), may be prepared by reacting an intermediate (XVII) with a carboxylic acid of formula (XVIII) or a functional derivative thereof.

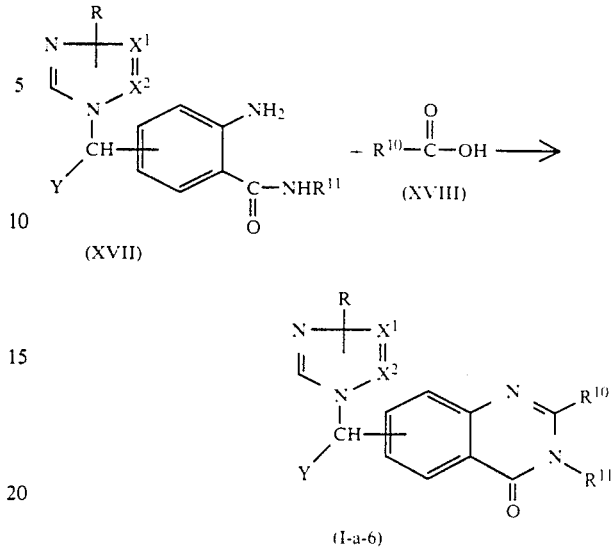

Said functional derivative of (XVIII) is meant to include the halide, anhydride, amide and ester form of (XVIII), including the ortho and imino ester form thereof. The cyclization is carried out according to similar procedures as described herein before for the preparation of (I-a-1) starting from (VIII) and (IX).

Alternatively, some compounds of formula (I) may also be prepared according to procedures analogous to those described in the literature for the preparation of azoles by cyclizing an appropriate starting material.

The compounds of formula (I-x) may also be prepared, for example, by cyclizing an intermediate of formula (XIX) and desulfurating the thus obtained intermediate of formula (XX).

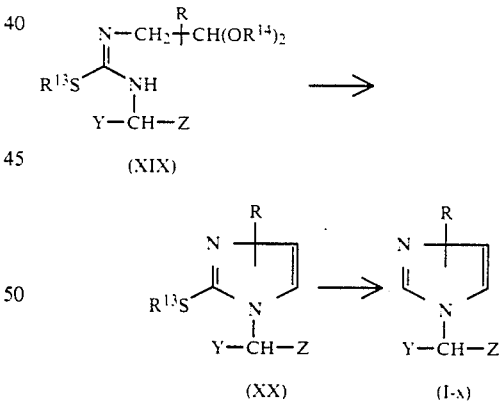

In formulae (XIX) and (XX) $R^{13}$ represents hydrogen or $C_{1-6}$alkyl and $R^{14}$ represents $C_{1-6}$alkyl or both $R^{14}$ taken together form a $C_{2-3}$alkanediyl radical.

Said cyclization reaction may conveniently be conducted by stirring and heating intermediate (XIX) in an aqueous acidic solvent, e.g. in aqueous hydrochloric or sulfuric acid. The intermediate (XX) may be desulfurated following art-known procedures, e.g., by treatment with Raney nickel in the presence of an alkanol, e.g. methanol, ethanol and the like, or by treatment with nitric acid, optionally in the presence of sodium nitrite.

The compounds of formula (I-y) may be prepared from a hydrazine derivative of formula (XXI) by reaction with s-triazine following the procedures described in J. Org. Chem., 1956, 1037.

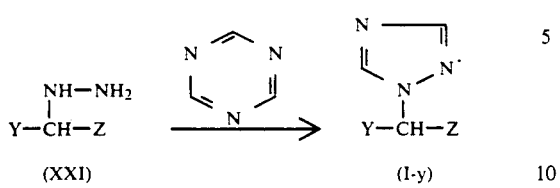

The intermediate hydrazine (XXI) and the corresponding intermediate amine of formula Y—CH(NH$_2$)—Z (XXII) may also advantageously be converted into azoles, wherein —X$^1$=X$^2$— is a bivalent radical of formula (x), (y) or (z), following the procedures described in U.S. Pat. No. 4,267,179, incorporated herein by reference.

The compounds of formula (I) can also be converted into each other following art-known functional group transformation procedures. For example, the compounds of formula (I-a-4) wherein R$^6$ and R$^7$ are both hydrogen may be converted into compounds of formula (I-a-3) wherein R$^5$ is halo by treatment with a halogenating agent such as, for example, phosphoryl chloride, thionylchloride, pentachlorophosphorane, sulfurylchloride and the like. The thus obtained compounds of formula (I-a-3) wherein R$^5$ is halo may further be converted into compounds wherein R$^5$ is C$_{1-6}$alkyloxy by reacting the starting compound with an appropriate alcohol, preferably an alkali metal or ·earth alkaline metal salt of said alcohol. According to the same functional group transformation reactions, the compounds of formula (I-a-2) wherein R$^3$ is hydrogen may be converted into the corresponding compounds of formula (I-a-1). The compounds of formula (I-a-3) can also be obtained by oxidizing a compound of formula (I-a-1) with an appropriate oxidizing reagent in a suitable reaction-inert solvent. Appropriate oxidizing reagents are, for example, permanganate or manganese(IV)oxide, silver oxide, silver nitrate, tert. butylhydroperoxide, hypochlorite, chromic acid, ferric chloride, ferric cyanide, lead tetra-acetate and the like. Suitable solvents for said oxidation reactions are, for example, water, alkanols, e.g. methanol, ethanol and the like, ketones, e.g. 2-propanone, 4-methyl-2-pentanone and the like, halogenated hydrocarbons, e.g. trichloromethane, tetrachloromethane and the like, ethers, e.g. 1,1'-oxybisethane, tetrahydrofuran, 1,4-dioxane and the like, dipolar aprotic solvents, e.g. N,N-dimethylformamide, N,N-dimethylacetamide, pyridine and the like, or a mixture of such solvents. Following analogous oxidation procedures the compounds of formula (I-a-4) may be obtained from the compounds of formula (I-a-2).

A number of intermediates and starting materials in the foregoing preparations are known compounds which may be prepared according to art-known methodologies of preparing said or similar compounds and some intermediates are new. Some intermediates of the previous reaction schemes are novel and have especially been developed for conversion into the compounds of the invention.

Intermediates of formula (III) and (V) wherein Y is other than hydrogen can be prepared from an appropriately substituted quinazoline derivative of formula (XXIII) according to the following reaction sequence.

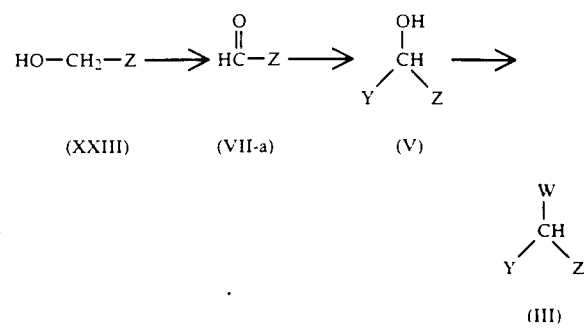

The hydroxymethyl moiety of formula (XXIII) is converted into a formyl moiety with a suitable oxidizing agent, e.g. manganese(IV)oxide or potassium permanganate, and subsequently reacted with a metal alkyl, e.g. methyllithium, butyllithium, metal aryl, e.g. phenyllithium, or with a complex metal alkyl or aryl in a suitable solvent such as, for example, an ether, e.g. tetrahydrofuran, 1,1'-oxybisethane and the like to form the secondary alcohols. The desired intermediates of formula (III) may then be obtained by converting the alcohol function of the intermediate of formula (V) into an appropriate leaving group W following standard procedures as known in the art. For example, halides are generally prepared by the reaction of (V) with an appropriate halogenating agent such as, for example, thionyl chloride, sulfuryl chloride, pentachlorophosphorane, pentabromophosphorane, phosphorylchloride, hydrochloric acid, hydrobromic acid and the like halogenating agents. The intermediates of formula (III) wherein Y is hydrogen can be obtained directly from the intermediates of formula (XXIII) following the procedure described hereinabove for converting (V) into (III).

Some intermediates of formula (III) wherein Y is other than hydrogen may also be prepared by acylating an intermediate quinazoline derivative of formula (XXIV) with an appropriate acylating reagent (XXV) according to art-known Friedel-Crafts acylation reaction procedures, reducing the obtained ketone (VII-b) with an appropriate reductant, e.g. sodium borohydride and the like in a suitable solvent such as an alcohol. e.g. methanol, ethanol or mixtures thereof with tetrahydrofuran and subsequently converting the alcohol function into an appropriate leaving group W as described hereinbefore.

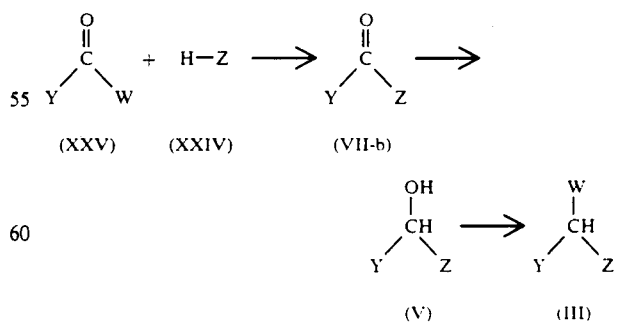

The intermediates of formula (VIII) can generally be prepared from amides, ureas or carbamates of formula (X-a) following art-known hydrolysis procedures, for example, by treating said amides, ureas or carbamates (X-a) with an acidic or basic aqueous solution, optionally at an enhanced temperature.

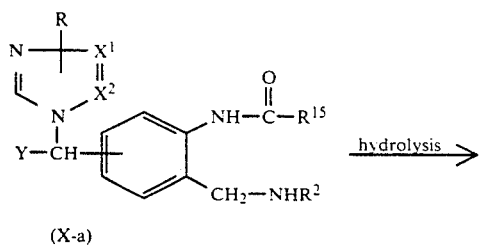

(X-a)

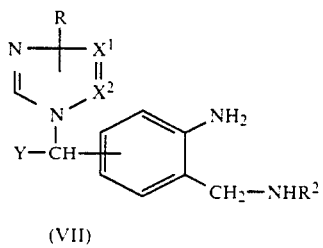

(VII)

In formula (X-a) and hereinafter $R^{15}$ represents either $C_{1-6}$alkyl, trifluoromethyl, $Ar^2$ or $Ar^2$-$C_{1-6}$alkyl; or $C_{1-6}$alkyloxy, amino or mono- or di($C_{1-6}$alkyl)amino.

The intermediates of formula (X-a) can be prepared by reducing an imine of formula (XII-a) following art-known reduction procedures such as, for example, reduction with an alkali metal borohydride, e.g. lithium, potassium, or preferably, sodium borohydride, sodium cyanoborohydride and the like reagents, in a reaction-inert solvent such as, for example, an alkanol, e.g. methanol, ethanol and the like.

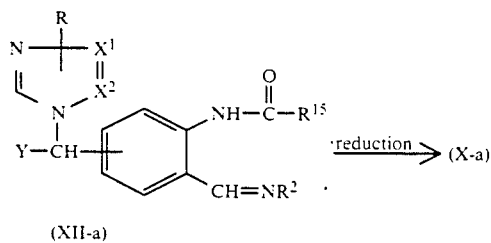

(XII-a)

The imines of formula (XII-a) in turn are prepared from an aldehyde of formula (XIII-a) by reaction with an amine of formula $R^2$—$NH_2$ in a reaction-inert solvent in the presence of an appropriate acid catalyst such as, for example, a sulfonic acid, e.g. methanesulfonic, benzenesulfonic, 4-methylbenzenesulfonic acid and the like acid catalysts.

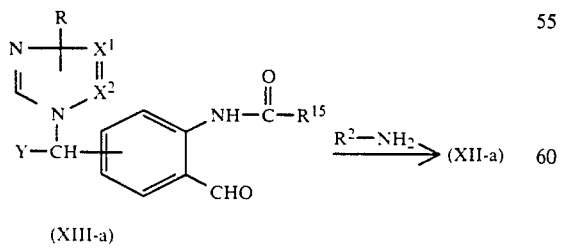

(XIII-a)

The aldehydes of formula (XIII-a) can prepared from a derivative of formula (XXVII) wherein P represents a protected carboxaldehyde group or a protected hydroxymethyl group, by hydrolysis of the protective group and in the case of the hydroxymethyl group, oxidation to the carboxaldehyde group.

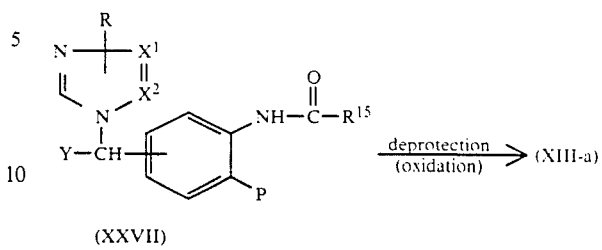

(XXVII)

Examples of suitable protective groups for hydroxymethyl are, for example, tetrahydropyranyl, 2-methoxyethoxymethyl, 2-methoxypropyl, 2-acetoxypropyl, 1-ethoxyethyl and the like; a trialkylsilyl group, e.g. trimethylsilyl, tert. butyldimethylsilyl and the like groups. Examples of suitable protective groups for carboxaldehyde are acyclic acetals formed with $C_{1-6}$alkanols such as methanol, ethanol and the like; or cyclic acetals formed with diols such as, 1,2-ethanediol, 1,3-propanediol and the like. Said deprotection reactions can easily be conducted following art-known methods of hydrolyzing acetals and silyl ethers, e.g. by acid hydrolysis in aqueous media.

Said oxidation of a hydroxymethyl to a carboxaldehyde group can conveniently be conducted by oxidation with a suitable oxidizing agent such as, for example, manganese (IV) oxide; permanganate salts, e.g. potassium permanganate; dimethylsulfoxide with a dehydrating reagent, e.g. oxalylchloride, sulfur trioxide, dicyclohexylcarbodiimide and the like. Suitable solvents for said oxidation are, for example, water, halogenated hydrocarbons, e.g. dichloromethane, trichloromethane, tetrachloromethane and the like.

The protected intermediates of formula (XXVII) are generally prepared from ketones of formula (XXVIII) following reaction sequences as described hereinabove for the conversion of ketones of formula (XXVI) into compounds of formula (I).

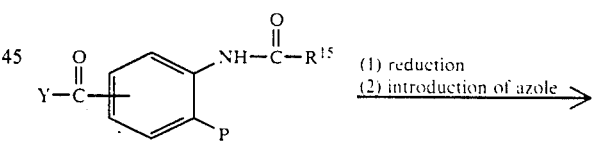

(XXVIII)

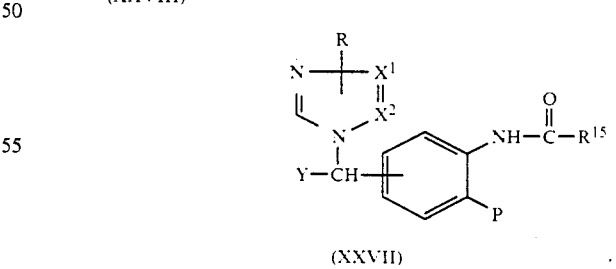

(XXVII)

The intermediates of formula (XXVIII) are obtained from a suitably substituted nitrobenzene (XXIX) by reduction following art-known nitro-to-amino reduction procedures, e.g. catalytic hydrogenation with Raney nickel, palladium-on-charcoal and the like; and subsequently acylating the thus obtained aniline with a $C_{1-6}$alkanoic halide or anhydride, a $C_{1-6}$alkylcarbonohalidate, e.g. ethyl carbonochloridate, 1,1.-dimethylethyl carbonochloridate and the like acylating reagents.

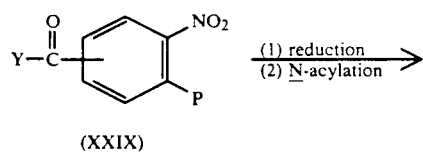

(XXIX)

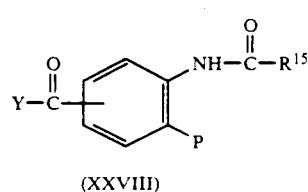

(XXVIII)

The intermediates of formula (XVI) wherein $R^8$ and $R^9$ are hydrogen or those of formula (XVII) wherein $R^{11}$ is hydrogen, said intermediates being represented by formula (XXXI), may, for example, be prepared from an appropriately substituted nitrobenzenamine of formula (XXX) by converting the latter into the corresponding nitrobenzenenitrile by diazotation and subsequent reaction with a cyanide salt e.g. copper cyanide and/or sodium cyanide, and reducing the thus obtained nitrobenzenenitrile under a hydrogen atmosphere, in the presence of an appropriate catalyst such as, for example, Raney nickel.

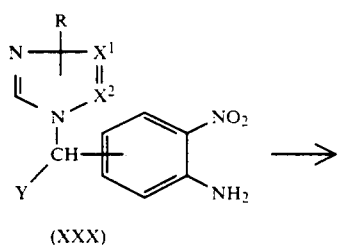

(XXX)

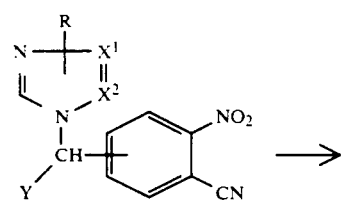

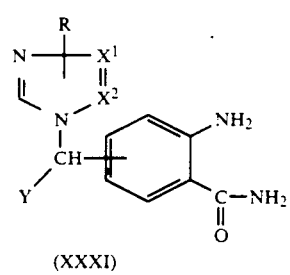

(XXXI)

The intermediates of formula (XXXI) can also be obtained from a ketone of formula (XXXII) following the reaction sequences as described hereinabove for the conversion of ketones of formula (XXVI) into compounds of formula (I).

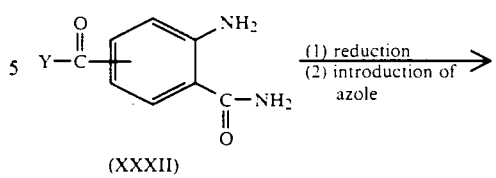

(XXXII)

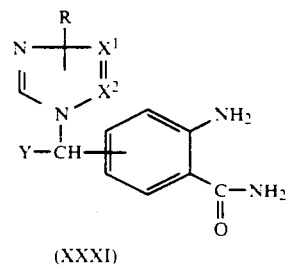

(XXXI)

The intermediate ketones of formula (XXXII) can be prepared from a suitably substituted 2-nitrobenzaldehyde of formula (XXXIII) by reacting the aldehyde with hydroxylamine or an acid addition salt thereof and dehydrating the intermediate oxime to a benzenenitrile of formula (XXXIV). The thus obtained nitrile is further hydrolyzed to an amide group and the nitro group reduced to an amino group following art-known hydrolysis and reduction procedures.

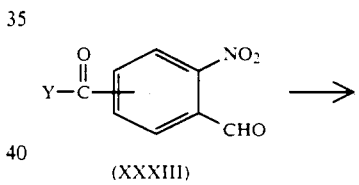

(XXXIII)

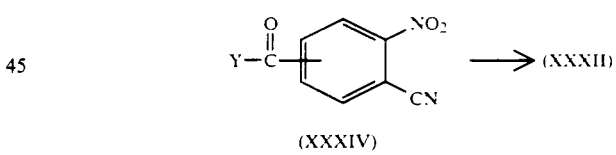

(XXXIV)

The intermediates of formula (XVII) and (XVI) wherein $R^8$ is hydrogen, said intermediates being represented by formula (XXXV) can alternatively be prepared from a ketone of formula (XXXVI) following the reaction sequences described hereinabove for the conversion of ketones of formula (XXVI) into compounds of formula (I).

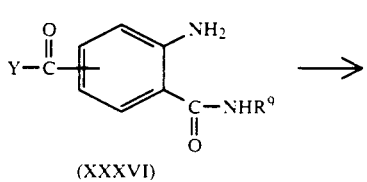

(XXXVI)

-continued

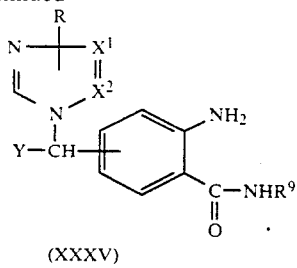

(XXXV)

The intermediates of formula (XXXVI) inturn can be obtained from a 2-nitrobenzoic acid of formula (XXXVII) by N-acylation of an amine $R^9$—$NH_2$ following art-known amidation procedures and reduction of the nitro group to an amino group according to procedures described hereinabove, for example, in the conversion of (XXIX) into (XXVIII).

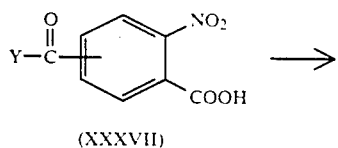

(XXXVII)

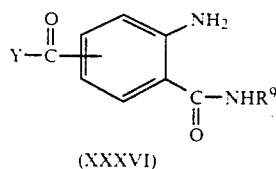

(XXXVI)

The intermediate hydrazines (XXI) and amines (XXII) may conveniently be prepared from a ketone of formula (XXVI) by reaction with either an acid addition salt thereof, or with hydroxylamine or hydrazine or an acid addition salt or a solvate thereof, and reducing the thus obtained oxime or hydrazone, for example, by catalytic hydrogenation in the presence of hydrogen and an appropriate hydrogenation catalyst, e.g. Raney nickel and the like.

The intermediates of formula (XIX) can be prepared from an amine of formula (XXII) by reaction with a reagent of formula (XXXVIII) and optionally S-alkylating the thus obtained thiourea with a $C_{1-6}$alkylhalide.

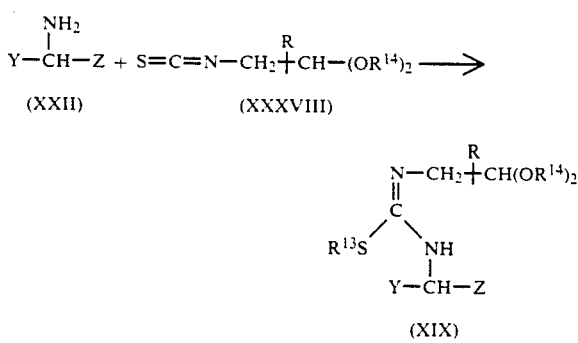

The compounds of formula (I) and some of the intermediates in this invention have an asymmetric carbon atom in their structure. This chiral center may be present in a R- and a S-configuration, this R- and S-notation being in correspondence with the rules described in Pure Appl. Chem., 1976, 45, 11–30.

Pure stereochemically isomeric forms of the compounds of this invention may be obtained by the application of art-known procedures. Diastereoisomers may be separated by physical separation methods such as selective crystallization and chromatographic techniques, e.g. counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

The compounds of the present invention, their pharmaceutically acceptable acid addition salts and their possible stereochemically isomeric forms have useful pharmacological properties. For example, they suppress the plasma elimination of retinoids, such as, all-trans-retinoic acid, 13-cis retinoic acid and their derivatives. The latter results in more sustained/higher tissue concentrations of retinoic acid and improved control of the differentiation and growth of various cell types. In addition some compounds inhibit the formation of androgens from progestines and/or inhibit the action of the enzyme complex aromatase which catalyses the formation of estrogens from androgenic steroids in mammals. A number of compounds also show an inhibitory action on the biosynthesis of thromboxane $A_2$.

Said property of the compounds of the invention to delay the metabolism of retinoic acid can easily be evidenced in various in vivo experiments. A particular test procedure is described hereinafter as the "Metabolism of endogenous or exogenously administered all-trans-retinoic acid" test and demonstrates the suppression of the plasma elimination of endogenous or exogenously administered all-trans-retinoic acid. As such, the compounds of formula (I) can be used to control the rate of growth and differentiation of various cell types which effects are known to be affected by retinoids. The ability of retinoids, such as, 13-cis-retinoic acid, all-trans-retinoic acid and their derivatives to modulate differentiation and proliferation in several cell types whether they are of epithelial or mesenchymal origin is extensively studied and reviewed in J. Clin. Chem. Clin. Biochem., 26, 479–488 (1983); Pharmacological Reviews 36, 935–1005, (1984), Arch. Dermatol. 117, 160–180; (1981) and Journal of Medicinal Chemistry 25, 1269–1277, (1982).

In view of their capability to delay the metabolism of retinoic acid the compounds can thus be used in the treatment of disorders which are characterized by an increased proliferation and/or abnormal differentiation of epithelial cells. In particular the compounds of the invention can be used for treatment of carcinoma which is essentially a derailment of cellular differentiation, occurring in epithelial tissues. Other uses include, in addition to cancer treatment, the treatment of a variety of disorders of keratinization such as, for example, acne, psoriasis, lamellar ichthyosis, plantar warts, callosities, acanthosis nigricans, lichen planus, molluscum, melasma, corneal epithelial abrasion, geographic tongue, Fox-Fordyce disease, cutaneous metastatic melanoma and keloids, epidermolytic hyperkeratosis, Darier's disease, pityriasis rubra pilaris, congenital ichthyosiform erythroderma, hyperkeratosis palmaris et plantaris, and similar diseases.

The anti-tumor activity may be demonstrated in several retinoic acid-sensitive and insensitive cell lines and solid tumors such as, for example, in Ta3-Ha induced mamma tumors in female mice.

The inhibition of androgen and/or estrogen formation can be demonstrated by analyzing the effects of the compounds of the invention on the conversion of progestins into androgens in the presence of testicular microsomes or on the conversion of androstenedione into estrone and estradiol in the presence of human placental microsomes. The in vivo-inhibition of androgen or estrogen formation can, for example, be demonstrated by measuring the suppression of the plasma testosterone or estrogen concentration in dogs, rats or mice. A number of relevant tests have been described in EP-A-260,744 and EP-A-293,978, which correspond to U.S. Pat. Nos. 4,859,684 and 4,943,574, respectively. In view of their capability to inhibit the biosynthesis of estrogens and/or androgens the compounds can be used in the treatment of estrogen or androgen dependent disorders such as, for example, breast cancer, endometriosis, endometrial cancer, polycystic ovarian disease, benign breast disease, prostatic cancer and hirsutism.

The beneficial effect of androgen inhibitors in these disorders, especially in the treatment of prostatic cancer, is described in, e.g., Journal of Urology 132, 61–63 (1984). The beneficial effect of aromatase inhibitors in these disorders, especially in the treatment of breast cancer, is described in, e.g. Cancer Research, 42, Suppl. 8:3261s (1982).

In view of the usefulness of the subject compounds it is evident that the present invention provides a method for treating mammals suffering from disorders which are characterized by an increased proliferation and/or abnormal differentiation of normal, preneoplastic or neoplastic cells, whether they are epithelial or mesenchymal; whether they are of ectodermal, endodermal or mesodermal origin; or whether they are estrogen dependent, androgen dependent or nonestrogen and nonandrogen dependent. Said method comprises the systemic or topical administration to the latter of an amount, effective to treat said disorders, of a compound of formula (I), a pharmaceutically acceptable acid-addition salt, or a possible stereochemically isomeric form thereof. In particular the present invention provides a method in which the growth and differentiation in said normal, preneoplastic and neoplastic cells is sensitive to the actions of retinoids.

Those of skill in treating disorders which are characterized by an excessive proliferation and/or abnormal differentiation of tissues could determine the effective amount from the test results presented hereinafter. In general it is contemplated than an effective amount would be from 0.001 mg/kg to 50 mg/kg body weight and more preferably from 0.01 mg/kg to 10 mg/kg body weight.

The subject compounds may be formulated into various pharmaceutical forms for administration purposes. As appropriate compositions there may be cited all compositions usually employed for systemically or topically administering drugs. To prepare the pharmaceutical compositions of this invention, an effective amount of the particular compound, optionally in acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

As appropriate compositions for topical application there may be cited all compositions usually employed for topically administering drugs, e.g., creams, gellies, dressings, shampoos, tinctures, pastes, ointments, salves, powders and the like. Application of said compositions may be by aerosol e.g. with a propellent such as nitrogen carbon dioxide, a freon, or without a propellent such as a pump spray, drops, lotions, or a semisolid such as a thickened composition which can be applied by a swab. In particular compositions, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powders packets, wafers, injectable solutions or suspensions, teaspoonfuls, tablespoonfuls and the like, and segregated multiples thereof.

Other such compositions are preparations of the cosmetic type, such as toilet waters, packs, lotions, skin milks or milky lotions. Said preparations contain, besides the active ingredient, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents.

Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrochloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxyethylene polyoxypropylene glycol (e.g. the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

For preparing ointments, creams, toilet waters, skin milks, and the like, typically from 0.01 to 10% in particular from 0.1 to 5% and more in particular from 0.2 to 2.5% of the active ingredient will be incorporated in said compositions. In ointments or creams, the carrier for example consists of 1 to 20%, in particular 5 to 15% of a humectant, 0.1 to 10% in particular from 0.5 to 5% of a thickener and water; or said carrier may consist of 70 to 99%, in particular 20 to 95% of a surfactant, and 0 to 20%, in particular 2.5 to 15% of a fat; or 80 to 99.9% in particular 90 to 99% of a thickener; or 5 to 15% of a surfactant, 2-15% of a humectant, 0 to 80% of an oil, very small (<2%) amounts of preservative, colouring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10–50% of oil, 1 to 10% of surfactant, 50–80% of water and 0 to 3% of preservative and/or perfume. In the afore-mentioned preparations, all % symbols refer to weight by weight percentage. The humectant, surfactant, oil, etc. . . referred to in said preparations may be any such component used in the cosmetic arts but preferably will be one or more of the components mentioned hereinabove. Further, when in the above compositions one or more of the components make up the major part of the composition, the other ingredients can evidently be not present at their indicated maximum concentration and therefore will make up the remainder of the composition.

Particular compositions for use in the method of the present invention are those wherein the active ingredient is formulated in liposome-containing compositions. Liposomes are artificial vesicles formed by amphiphatic molecules such as polar lipids, for example, phosphatidyl cholines, ethanolamines and serines, sphingomyelins, cardiolipins, plasmalogens, phosphatidic acids and cerebiosides. Liposomes are formed when suitable amphiphathic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If water-soluble materials are included in the aqueous phase during the swelling of the lipids they become entrapped in the aqueous layer between the lipid bilayers.

In a further aspect of the invention there are provided particular pharmaceutical or cosmetical compositions which comprise an inert carrier, an effective amount of a compound of formula (I) an acid addition salt or a stereochemically isomeric form thereof and an effective amount of a retinoic acid, a derivative thereof or a stereochemically isomeric form thereof. Said retinoic acid containing compositions are particularly useful for treating acne or for retarding the effects of aging of the skin and generally improve the quality of the skin, particularly human facial skin. A pharmaceutical or cosmetical composition containing retinoic acid or a derivative thereof as the active ingredient in intimate admixture with a dermatologically acceptable carrier can be prepared according to conventional compounding techniques, such as those known for topical application of retinoic acid and its derivatives. Conventional pharmaceutical compounding techniques for topical application of retinoic acid are described for example in, U.S. Pat. Nos. 3,906,108 and 4,247,547, which are incorporated herein by reference. Preferred composition for topical application are in form of a cream, ointment or lotion comprising from 0.005 to 0.5% (particularly from 0.01 to 0.1%) all-trans-retinoic acid, 13-cis-retinoic acid or a derivative thereof and from 0.1 to 5% of a compound of formula (I) and, a dermatologically acceptable acid addition salt thereof or a stereochemically isomeric form thereof, in a semi-solid or liquid diluent or carrier. These preferred compositions should preferably be non-irritating and as far as possible they should be odorless and non-toxic. For convenience in applying to the skin, the composition usually contain, besides water or an organic solvent, several of certain organic emollients, emulsifiers for the aqueous and/or non aqueous phases of the compositions, wetting agents preservatives and agents that facilitate the penetration and remainence of the active agents in the skin.

The following examples are intended to illustrate and not to limit the scope of the present invention. Unless otherwise stated all parts therein are by weight.

EXPERIMENTAL PART

A. Preparation of the Intermediates

EXAMPLE 1

To a vigorously stirred amount of 45 parts of aluminum chloride were added dropwise 7.05 parts of N,N- dimethylformamide. After stirring for 5 min. at 70° C., there were added 5 parts of benzoyl chloride and, dropwise, 4.7 parts of 3,4-dihydro-2(1H)-quinazolinone. Stirring was continued for 2 hours at 70° C. The reaction mixture was poured into ice-water and there were added 63.5 parts of HCl. The precipitate was filtered off and recrystallized from 2-methoxyethanol, yielding 6.5 parts (76.4%) of 6-benzoyl-3,4-dihydro-2(1H)-quinazolinone; mp. 264.8° C. (interm. 1).

In a similar manner there were also prepared the intermediates listed in Table 1.

TABLE 1

R—C(=O)—[phenyl]—C(=NH)(X)—NH (with H—N)

| Interm. No. | R | X | Physical data (mp. in °C.) |
|---|---|---|---|
| 2 | (3-pyridinyl) | O | 256.4/.HCl |
| 3 | 3-ClC$_6$H$_4$ | O | >260 (decomp.) |
| 4 | i.C$_3$H$_7$ | O | 291.0 |
| 5 | CH$_3$ | O | 240.1 |
| 6 | c.C$_3$H$_5$ | O | 269.3 |
| 7 | C$_6$H$_5$ | S | 264.7 |

EXAMPLE 2 a) A mixture of 14.7 parts of 5-chloro-2-nitrobenzaldehyde, 13.3 parts of thrimethoxymethane, 0.15 parts of 4-methylbenzenesulfonic acid and 64 parts of 2-propanol was stirred at reflux temperature until completion of the reaction. After cooling, there was added Na$_2$CO$_3$ and stirring was continued for 5 min. The reaction mixture was filtered and the filtrate was evaporated, yielding 18.3 parts (99.7%) of 4-chloro-2-(dimethoxymethyl)-1-nitrobenzene (interm. 8).

b) To a solution of 9.55 parts of benzeneacetonitrile in 90 parts of N,N-dimethylacetamide were added 7.6 parts of a dispersion of sodium hydride in mineral oil (50%). The mixture was stirred until H$_2$-evolution ceased. Then there were added 1.28 parts of 2-(2-methoxyethoxy)-N,N-bis[2-(2-methoxyethoxy)ethyl]-ethanamine and, dropwise, a solution of 18.3 parts of intermediate 8, namely 4-chloro-2-(dimethoxymethyl)-1-nitrobenzene, in 27 parts of N,N-dimethylacetamide. The whole was stirred at room temperature for a while and was then poured into ice-water. After neutralizing, the product was extracted with dichloromethane. The extract was dried, filtered and evaporated, yielding 28.1 parts (100%) of 3-(dimethoxymethyl)-4-nitro-α-phenylenzeneacetonitrile (interm. 9).

c) A mixture of 26.7 parts of intermediate 9, namely 3-(dimethoxymethyl)-4-nitro-α-phenylbenzeneacetonitrile, 12.3 parts of potassium carbonate and 360 parts of N,N-dimethylacetamide was stirred at room temperature while bubbling air through it. The reaction mixture was poured into water and the whole was extracted with dichloromethane. The extract was dried, filtered and evaporated and the residue was purified by column chromatography (silica gel; CHCl$_3$/hexane 80:20). The eluent of the desired fraction was evaporated, yielding 18.1 parts (67.3%) of [3-(dimethoxymethyl)-4-nitrophenyl]phenylmethanone (interm. 10).

d) A mixture of 19 parts of intermediate 10, namely [3-(dimethoxymethyl)-4-nitrophenyl]phenylmethanone, 40 parts of an aqueous hydrochloric acid solution 5N and 120 parts of trichloromethane was stirred overnight at room temperature and for 4 hours at reflux temperature. After cooling, the organic layer was separated, basified with NH$_4$OH (aq.), washed with water, dried, filtered and evaporated. The residue was crystallized from a mixture of 2,2'-oxybispropane and ethyl acetate. The product was filtered off, washed successively with a mixture of 2,2'-oxybispropane and ethyl acetate and with 2,2'-oxybispropane and dried in vacuo at 50° C., yielding 7.61 parts (49.0%) of 5-benzoyl-2-nitrobenzaldehyde; mp. 96.7° C. (interm. 11).

e) A mixture of 19 parts of intermediate 11, namely 5-benzoyl-2-nitrobenzaldehyde, 6.18 parts of hydroxylamine monohydrochloride, 474 parts of ethanol and 7.76 parts of sodium hydrogen carbonate was refluxed for 14 hours. The reaction mixture was filtered and the filtrate was evaporated. The residual oil was stirred in water. The solid was filtered off and recrystallized from a mixture of ethyl acetate and hexane. The product was filtered off, washed successively with a mixture of ethyl acetate and hexane and with 2,2'-oxybispropane and dried in vacuo at 60° C., yielding 16.6 parts (82.4%) of (E+Z)-5-benzoyl-2-nitrobenzaldehyde, oxime: mp. 135.0° C. (interm. 12).

f) A mixture of 17.5 parts of intermediate 12, namely (E+Z)-5-benzoyl-2-nitrobenzaldehyde, oxime, and 162 parts of acetic anhydride was refluxed for 48 hours. The reaction mixture was evaporated and the residue was taken up in water. After basifying with NaHCO$_3$, the product was extracted with dichloromethane. The extract was dried, filtered and evaporated and the residue was purified by column chromatography (silica gel; CHCl$_3$/hexane 80:20). The eluent of the desired fraction was evaporated and the residue was co-evaporated with ethyl acetate. The product was crystallized successively from a mixture of ethyl acetate and 2,2'-oxybispropane and from ethyl acetate. The product was filtered off, washed with a mixture of ethyl acetate and 2,2'-oxybispropane and dried in vacuo at 50° C., yielding 5.30 parts (32.4%) of 5-benzoyl-2-nitrobenzonitrile; mp. 121.8° C. (interm. 13).

g) A solution of 8.9 parts of intermediate 13, namely 5-benzoyl-2-nitrobenzonitrile, 166 parts of sulfuric acid and 10 parts of water was heated at 90° C. for 1¾ hours. The reaction mixture was poured into ice-water. The precipitate was filtered off and recrystallized from methanol. The product was filtered off, washed with methanol and 2,2'-oxybispropane and dried in vacuo at 60°–70° C., yielding 5.23 parts (54.8%) of 5-benzoyl-2-nitrobenzamide; mp. 244.3° C. (intermediate 14).

h) A mixture of 7.76 parts of intermediate 14, namely 5-benzoyl-2-nitrobenzamide, 2 parts of a solution of thiophene in methanol 4% and 198 parts of methanol was hydrogenated overnight at normal pressure and at 50° C. with 2 parts of palladium-on-charcoal catalyst 10%. The catalyst was filtered off and washed with tetrahydrofuran. The combined filtrates were evaporated and the residue was co-evaporated with methylbenzene. The residue was purified by column chromatography (silica gel; CHCl$_3$/CH$_3$OH/CH$_3$OH(NH$_3$) 90:5:5). The eluent of the desired fraction was evaporated and the residue was taken up in methanol. This solution was concentrated and the product was filtered off, washed with methanol and 2,2'-oxybispropane and dried in vacuo at 60° C., yielding 2.84 parts (41.0%) of 2-amino-5-benzoylbenzamide; mp. 225.2° C. (interm. 15).

i) A mixture of 5 parts of intermediate 15, namely 2-amino-5-benzoylbenzamide, 5.53 parts of trimethoxymethane and 61 parts of formic acid was refluxed for 4–5 hours. The reaction mixture was evaporated and the residue was taken up in water. After basifying with NH₄OH (aq.), the product was extracted with a mixture of CHCl₃, CH₃OH and CH₃OH(NH₃) (90:5:5). The extract was dried, filtered and evaporated and the residue was crystallized from acetonitrile. The solid was filtered off* and purified by column chromatography (silica gel; CHCl₃/CH₃OH 95:5). The eluent of the desired fraction was evaporated and the residue was stirred in ethyl acetate. The product was filtered off, washed with ethyl acetate and 2,2'-oxybispropane and dried in vacuo at 70° C., yielding 0.53 parts (10.1%) of product; mp. 215.5° C. *The mother liquor was evaporated and the residue was treated similarly as above, yielding an additional 0.69 parts (13.2%) of product; mp. 214.3° C. Total yield: 1.22 parts (23.3%) of 6-benzoyl-4(3H)-quinazolinone (interm. 16).

EXAMPLE 3 a) To a solution of 22.8 parts of potassium hydroxide, 39.2 parts of pyridine and 89 parts of tetrahydrofuran were added 11.7 parts of benzeneacetonitrile and 16.7 parts of 2-nitrobenzoic acid. After stirring for 2 hours at room temperature, the reaction mixture was diluted with 200 parts of water while cooling on ice. The whole was acidified with HCl and then the tetrahydrofuran layer was separated. There were added 183 parts of 2,2'-oxybispropane and the mixture was stirred overnight. The precipitate was filtered off and dried, yielding 12.7 parts (47.7%) of product. Evaporation of the filtrate yielded an additional 17 parts (63.8%) of product. Total yield: 29.7 parts (100%) of 3-(cyanophenylmethylene)-6-(hydroxyimino)-1,4-cyclohexadiene-1-carboxylic acid; mp. 230.7° C. (intermediate 17).

b) To a solution of 16.2 parts of potassium hydroxide, 150 parts of water and 5.72 parts of intermediate 17, namely 3-(cyanophenylmethylene)-6-(hydroxyimino)-1,4-cyclohexadiene-1-carboxylic acid, was added a solution of 16.25 parts of hydrogen peroxide in 16 parts of water. After stirring for 1 hour at room temperature, the reaction mixture was acidified with HCl while cooling on ice. The product was extracted with dichloromethane and the extract was dried, filtered and evaporated. The residue was recrystallized from methylbenzene, yielding 3.7 parts (63.5%) of 5-benzoyl-2-nitrobenzoic acid; mp. 168.6° C. (interm. 18).

c) To solution of 8.5 parts of intermediate 18, namely 5-benzoyl-2-nitrobenzoic acid, in 66.5 parts of dichloromethane were added 5.3 parts of 1,1'-carbonylbis[1H-imidazole]. After stirring for 1 hour at room temperature, there were added 9.8 parts of benzenemethanamine. Stirring at room temperature was continued for 8 hours. The reaction mixture was diluted with 100 parts of water and acidified with HCl. The organic layer was separated, dried, filtered and evaporated. The residue was purified twice by column chromatography (silica gel; CHCl₃/CH₃OH 98:2; CH₃COOC₂H₅/C₆H₅CH₃ 10:90). The eluent of the desired fractions was evaporated and the residue was crystallized from methylbenzene, yielding 8.1 parts (72.5%) of 5-benzoyl-2-nitro-N-(phenylmethyl)benzamide; mp. 167.4° C. (interm. 19).

d) A mixture of 6 parts of intermediate 18, namely 5-benzoyl-2-nitrobenzoic acid, 5.24 parts of thionyl chloride and 89.4 parts of trichloromethane was stirred for 1 hour at reflux temperature. The reaction mixture was used as such for further synthesis. Yield: 6.37 parts (100%) of 5-benzoyl-2-nitrobenzoyl chloride (interm. 20).

e) Methanamine was bubbled through a solution of 23.17 parts of intermediate 20, namely 5-benzoyl-2-nitrobenzoyl chloride, in 178 parts of tetrahydrofuran at 0° C. for 15 min. and at room temperature for 30 min. The reaction mixture was evaporated and the residue was stirred with HCl 1N for 1 hour. The product was extracted with dichloromethane and the extract was dried, filtered and evaporated. The residue was purified by column chromatography (silica gel; CHCl₃/CH₃OH 98:2). The eluent of the desired fraction was evaporated and the residue was crystallized from methylbenzene, yielding 7 parts (30.8%) of 5-benzoyl-N-methyl-2-nitrobenzamide; mp. 137.6° C. (interm. 21).

f) A mixture of 6.5 parts of intermediate 21, namely 5-benzoyl-N-methyl-2-nitrobenzamide, 2 parts of a solution of thiophene in methanol 4% and 97 parts of 2-methoxyethanol was hydrogenated at normal pressure and at 50° C. with 2 parts of palladium-on-charcoal catalyst 10%. After the calculated amount of hydrogen was taken up, the catalyst was filtered off and the filtrate was evaporated. The residue was recrystallized from 2-propanol, yielding 4.64 parts (79.3%) of 2-amino-5-benzoyl-N-methylbenzamide; mp. 140.5° C. (interm. 22).

g) A solution of 5.3 parts of intermediate 22, namely 2-amino-5-benzoyl-N-methylbenzamide, 4 parts of 1,1'-carbonylbis[1H-imidazole], 107 parts of tetrahydrofuran and a catalytic amount of sodium hydride was stirred for 17 hours at reflux temperature. The precipitate was filtered off and dried in vacuo, yielding 3.5 parts (59.5%) of product. The filtrate was evaporated and the residue was washed with water and ethyl acetate and dried, yielding an additional 1.5 parts (25.5%) of product. Total yield: 5.0 parts (85.0%) of 6-benzoyl-3-methyl-2,4-(1H,3H)-quinazolinedione; mp. 250.6° C. (interm. 23).

In a similar manner there were also prepared:

6-benzoyl-2,4(1H,3H)-quinazolinedione; mp. >300° C. (interm. 24).

6-benzoyl-3-(phenylmethyl)-2,4(1H,3H)-quinazolinedione; mp. 237.9° C. (interm. 25).

6-benzoyl-2,3-dihydro-3-(phenylmethyl)-2-thioxo-4(1H)-quinazolinone; mp. 255.1° C. (interm. 26).

EXAMPLE 4

To a mixture of 4.35 parts of intermediate 2, namely 3,4-dihydro-6-(3-pyridinylcarbonyl)-2(1H)-quinazolinone monohydrochloride, 63.2 parts of methanol, 1.2 parts of sodium hydroxide and 15 parts of water were added portionwise 0.6 parts of sodium tetrahydroborate. After stirring for 2 hours at room temperature, there was added a mixture of 2.1 parts of acetic acid in 25 parts of water. The precipitate was filtered off, washed with water, 2-propanol and 1,1'-oxybisethane and dried, yielding 3.7 parts (96.6%) of 3,4-dihydro-6-[hydroxy(3-pyridinyl)methyl]-2(1H)-quinazolinone; mp. 272.0° C. (interm. 27).

In a similar manner there were also prepared the intermediates listed in Tables 2 and 3.

TABLE 2

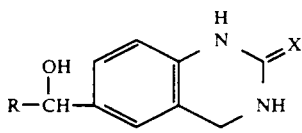

| Interm. No. | R | X | Physical data (mp. in °C.) |
|---|---|---|---|
| 28 | C₆H₅ | O | 214.3 |
| 29 | 3-ClC₆H₄ | O | 266.4 |
| 30 | i.C₃H₇ | O | 274.9 |
| 31 | CH₃ | O | 275.5 |
| 32 | C₆H₅ | S | 239.7 |
| 33 | c.C₃H₅ | O | 225 |

TABLE 3

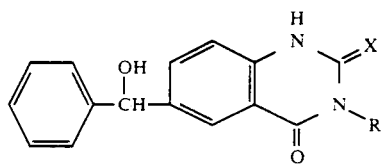

| Interm. No. | R | X | Physical data (mp. in °C.) |
|---|---|---|---|
| 34 | CH₂—C₆H₅ | O | 191.8 |
| 35 | CH₂—C₆H₅ | S | 178.1 |
| 36 | H | O | — |
| 37 | CH₃ | O | 261.0 |

In a similar manner there was also prepared:
6-(hydroxyphenylmethyl)-4(3H)-quinazolinone; mp. 204.8° C. (interm. 38).

EXAMPLE 5

A mixture of 3 parts of intermediate 27, namely 3,4-dihydro-6-[hydroxy(3-pyridinyl)methyl]-2(1H)-quinazolinone, and 40.5 parts of thionyl chloride was stirred for 10 min. at room temperature and for 15 min. at reflux temperature. The reaction mixture was evaporated and the residue was co-evaporated with methylbenzene. The residue was dried in vacuo at 60° C. for 24 hours, yielding 3.1 parts (99.9%) of 6-[chloro(3-pyridinyl)methyl]-3,4-dihydro-2(1H)-quinazolinone monohydrochloride (intermediate 39).

In a similar manner there were also prepared the intermediates listed in Tables 4 and 5.

TABLE 4

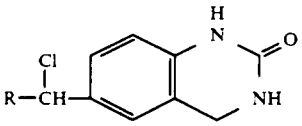

| Interm. No. | R | Physical data (mp. in °C.) |
|---|---|---|
| 40 | C₆H₅ | — |
| 41 | i.C₃H₇ | .HCl |
| 42 | CH₃ | .HCl |
| 43 | 3-ClC₆H₄ | — |

TABLE 5

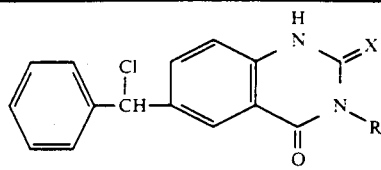

| Interm. No. | R | X | Physical data (mp. in °C.) |
|---|---|---|---|
| 44 | CH₂—C₆H₅ | S | — |
| 45 | H | O | — |
| 46 | CH₂—C₆H₅ | O | — |
| 47 | CH₃ | O | — |

EXAMPLE 6

A mixture of 4 parts of intermediate 38, namely 6-(hydroxyphenylmethyl)-4(3H)-quinazolinone, and 67.7 parts of a solution of hydrobromic acid in acetic acid 30% was stirred for 24 hours at room temperature. The reaction mixture was evaporated and the residue was co-evaporated with methylbenzene, yielding 6.5 parts (100%) of 6-(bromophenylmethyl)-4(3H)-quinazolinone monohydrobromide (interm. 48).

In a similar manner there were also prepared:
6-(bromophenylmethyl)-3-(phenylmethyl)-2,4(1H,3H)-quinazolinedione (interm. 49).
6-(bromophenylmethyl)-3,4-dihydro-2(1H)-quinazolinethione (interm. 50).

EXAMPLE 7 a) To a stirred solution of 7.5 parts of 4-amino-3-nitro-α-phenylbenzenemethanol, 0.1 parts of a dispersion of sodium hydride in mineral oil (50%) and 90 parts of tetrahydrofuran were added 6.4 parts of 1,1'carbonylbis[1H-imidazole]. After stirring for 1 hour at reflux temperature, the reaction mixture was evaporated. The residue was purified by column chromatography (silica gel; CHCl₃/CH₃OH 93:7). The eluent of the desired fraction was evaporated and the residue was crystallized from methylbenzene. The product was dried for 2 hours at 80° C., yielding 6.33 parts (71%) of 4-[(1-H-imidazol-1-yl)phenylmethyl]-2-nitrobenzenamine (interm. 51).

b) To 200 ml of cooled (0°-5° C.) HCl 5N were added 19.3 parts of intermediate 51, namely 4-[(1H-imidazol-1-yl)phenylmethyl]-2-nitrobenzenamine, while stirring. When a homogeneous solution was obtained, there was added dropwise a solution of 4.75 parts of sodium nitrite in 40 parts of water at 0°-5° C. Stirring at 0°-5° C. was continued for ½ hour and then the mixture was added dropwise to a cooled (0°-5° C.) solution of 5.8 parts of copper(I)cyanide, 6.42 parts of sodium cyanide and 127.1 parts of Na₂CO₃ (aq.) in a mixture of 700 parts of water and 298 parts of trichloromethane. The whole was left overnight to warm up to room temperature and then there were added NH₄OH (aq.) and 447 parts of trichloromethane. After heating at 50° C. for 15 min. and subsequent cooling, the organic layer was separated, dried, filtered and evaporated. The residue was purified twice by column chromatography (silica gel; CHCl₃/CH₃OH (NH₃) 97.5:2.5; CHCl₃/CH₃OH 97.5:2.5). The eluent of the desired fractions was evaporated, yielding 14.6 parts (73.2%) of 4-[(1H-imidazol-1-yl)phenylmethyl]-2-nitrobenzonitrile (interm. 52).

c) A solution of 6 parts of intermediate 52, namely 4-[(1H-imidazol-1-yl)phenylmethyl]-2-nitrobenzonitrile, in 316 parts of methanol saturated with ammonia was hydrogenated at room temperature and normal pressure with 3 parts of Raney nickel. After the calculated amount of hydrogen was taken up, the catalyst was filtered off and the filtrate was evaporated. The residue was co-evaporated with a mixture of methanol and methylbenzene, yielding 4.8 parts (82.9%) of 2-amino-4-[(1H-imidazol-1-yl)phenylmethyl]benzamide (interm. 53).

EXAMPLE 8 a) A mixture of 25 parts of 5-chloro-2-nitrobenzenemethanol, 13.3 parts of 3,4-dihydro-2H-pyran, 0.28 parts of dichloromethane and 300 parts of 4-methylbenzenesulfonic acid was stirred and for 2 hours at reflux temperature. After cooling, there was added $Na_2CO_3$ and the whole was stirred for 10 min. The reaction mixture was filtered and the filtrate was evaporated. The residue was co-evaporated with methylbenzene and was further purified by column chromatography (silica gel; $CHCl_3$). The eluent of the desired fraction was evaporated and the residue was co-evaporated with methylbenzene, yielding 36 parts (99.6%) of 2-[(5-chloro-2-nitrophenyl)methoxy]-tetrahydro-2H-pyran (interm. 54).

b) To a mixture of 7.13 parts of a dispersion of sodium hydride in mineral oil (50%) and 94 parts of N,N-dimethylacetamide was added dropwise a solution of 9.1 parts of benzeneacetonitrile in 18.8 parts of N,N-dimethylacetamide. After the hydrogen evolution had ceased, there were added 1.28 parts of tris-2,2,2-(2-methoxyethoxy)ethanamine and a solution of 20.2 parts of intermediate 54, namely 2-[(5-chloro-2-nitrophenyl)-methoxy]-tetrahydro-2H-pyran, in 28.2 parts of N,N-dimethylacetamide. After 15 minutes, the reaction mixture was poured into ice-water and the whole was neutralized. The product was extracted with dichloromethane and the extract was dried, filtered and evaporated, yielding 26.2 parts (100%) of 4-nitro-α-phenyl-3-[[(tetrahydro-2H-pyran-2-yl)oxy]methyl]benzeneacetonitrile (interm. 55).

c) A mixture of 26.2 parts of intermediate 55, namely 4-nitro-α-phenyl-3-[[(tetrahydro-2H-pyran-2-yl)oxy]-methyl]benzeneacetonitrile, 10.2 parts of potassium carbonate and 376 parts of N,N-dimethylacetamide was stirred at room temperature while air was bubbled through. The reaction mixture was poured into water and the product was extracted with 2,2'-oxybispropane. The extract was dried, filtered and evaporated, yielding 25 parts (98.6%) of [4-nitro-3-[[(tetrahydro-2H-pyran-2-yl)oxy]methyl]phenyl] phenylmethanone (interm. 56).

d) A mixture of 20 parts of intermediate 56, namely [4-nitro-3-[[(tetrahydro-2H-pyran-2-yl)oxy]methyl]phenyl] phenylmethanone, 2 parts of a solution of thiophene in methanol 4% and 395 parts of methanol was hydrogenated overnight at normal pressure and room temperature with 2 parts of palladium-on-charcoal catalyst 10%. Tetrahydrofuran was added to dissolve the precipitated reaction product. The catalyst was filtered off and the filtrate was evaporated. The residue was recrystallized from methanol. The product was filtered off, washed with methanol and 2,2'-oxybispropane and dried in vacuo at 60° C., yielding 14.93 parts (82.0%) of [4-amino-3-[[(tetrahydro-2H-pyran-2-yl)oxy]methyl]-phenyl] phenylmethanone; mp. 164.0° C. (interm. 57).

e) To a stirred and cooled (10° C.) solution of 13.7 parts of intermediate 57, namely [4-amino-3-[[(tetrahydro-2H-pyran-2-yl)oxy]methyl]phenyl] phenylmethanone, in 147 parts of pyridine were added dropwise 7.14 parts of ethyl chloroformate. After stirring for 1 hour at 10° C., the reaction mixture was poured into 700 parts of water. The product was extracted with dichloromethane and the extract was washed with water (3×), dried, filtered and evaporated. The residue was co-evaporated with ethanol (3×) and was then crystallized from ethanol. The product was filtered off, washed with ethanol and 2,2'-oxybispropane and dried in vacuo at 60° C., yielding 14.05 parts (83.5%) of ethyl [4-benzoyl-2-[[(tetrahydro-2H-pyran-2-yl)oxy]methyl]phenyl]carbamate; mp. 115.9° C. (interm. 58).

f) To a solution of 2 parts of intermediate 58, namely ethyl [4-benzoyl-2-[[(tetrahydro-2H-pyran-2-yl)oxy]-methyl]phenyl]carbamate, 11.9 parts of ethanol and 22.3 parts of tetrahydrofuran were added 0.2 parts of sodium tetrahydroborate. The mixture was stirred at room temperature for 1 hour and at 40°-50° C. until completion of the reaction. The solvent was evaporated and the residue was taken up in water. The product was extracted with dichloromethane and the extract was dried, filtered and evaporated. The residue was co-evaporated with methylbenzene and was used as such for further reaction. Yield: 2 parts (100%) of ethyl [4-(hydroxyphenylmethyl)-2-[[(tetrahydro-2H-pyran-2-yl)oxy]methyl]phenyl]carbamate. (interm. 59).

g) To a refluxing solution of 2 parts of intermediate 59, namely ethyl [4-(hydroxyphenylmethyl)-2-[[(tetrahydro-2H-pyran-2-yl)oxy]methyl]phenyl]carbamate, in 33.3 parts of dichloromethane was added dropwise a solution of 1.8 parts of 1,1'-carbonyl-bis[1H-imidazole] in 20 parts of dichloromethane. After stirring for 3 days at reflux temperature, the reaction mixture was cooled and washed with water (2×). The organic layer was dried, filtered and evaporated. The residue was purified by column chromatography (silica gel; $CHCl_3/C_2H_5OH$ 98:2). The eluent of the desired fraction was evaporated and the residue was left to crystallize. The crystallized product was filtered off, stirred in hexane and dried in vacuo, yielding 0.67 parts (41.1%) of ethyl [4-[(1H-imidazol-1-yl)phenylmethyl]-2-[[(tetrahydro-2H-pyran-2-yl)oxy]methyl]-phenyl]carbamate; mp. 132.2° C. (interm. 60).

h) A solution of 10.5 parts of intermediate 60, namely ethyl [4-[(1H-imidazol-1-yl)phenylmethyl]-2-[[(tetrahydro-2H-pyran-2-yl)oxy]methyl]phenyl]carbamate, 5.5 parts of 4-methylbenzenesulfonic acid and 198 parts of ethanol was stirred over weekend at room temperature and for a short time at 50°-60° C. After cooling, there were added ethanol and $Na_2CO_3$. The whole was stirred for 15 min. and was then filtered. The filtrate was evaporated and the residue was partitioned between dichloromethane and water. The organic layer was separated and the aqueous layer was re-extracted with dichloromethane. The combined dichloromethane layers were dried, filtered and evaporated. The residue was purified by column chromatography (silica gel; $CHCl_3/CH_3OH$ 95:5). The eluent of the desired fraction was evaporated and the residue was co-evaporated with methylbenzene. The crystallized product was filtered off, stirred in 2,2'-oxybispropane and dried in vacuo, yielding 4.65 parts (46.0%) of ethyl [2-(hydroxymethyl)-4-[(1H-imidazol-1-yl)phenylmethyl]phenyl]-carbamate; mp. 143.1° C. (interm. 61).

i) To a solution of 5.9 parts of intermediate 61, namely ethyl [2-(hydroxymethyl)-4-[(1H-imidazol-1-yl)phenylmethyl]phenyl]carbamate, in 798 parts of dichloromethane were added 21.5 parts of manganese(IV)oxide and a catalytic amount of KMnO₄. After stirring for 18 hours at room temperature, the reaction mixture was filtered over diatomaceous earth and the filtrate was evaporated. The residue was co-evaporated with methylbenzene and was further purified by column chromatography (silica gel; CHCl₃/CH₃OH 95:5). The eluent of the desired fraction was evaporated and the residue was taken up in ethyl acetate. This solution was concentrated and left to crystallize. The crystallized product was filtered off, stirred in 2,2'-oxybispropane and dried in vacuo, yielding 2.85 parts (48.8%) of ethyl [2-formyl-4-[(1H-imidazol-1-yl)phenylmethyl]phenyl]carbamate; mp. 107.0° C. (interm. 62).

j) A solution of 2 parts of intermediate 62, namely ethyl [2-formyl-4-[(1H-imidazol-1-yl)phenylmethyl]phenyl]carbamate in 32.4 parts of 1-butanol were added to the residue. The whole was stirred at room temperature overnight while saturating with methanamine. The solvent was evaporated and the residue was co-evaporated with methylbenzene, yielding 1.7 parts (82.3%) of ethyl [4-[(1H-imidazol-1-yl)phenyl-methyl]-2-[(methylimino)methyl]phenyl]carbamate (interm. 63).

EXAMPLE 9 a) A mixture of 68 parts of intermediate 10, namely [3-(dimethoxymethyl)-4-nitrophenyl] phenylmethanone, 4 parts of a solution of thiophene in methanol 4%, 20 parts of calcium oxide and 474 parts of methanol was hydrogenated for 24 hours at normal pressure and room temperature with 6 parts of palladium-on-charcoal catalyst 10%. The catalyst was filtered off and the filtrate was evaporated. The residue was co-evaporated with methylbenzene, yielding 59.1 parts (96.8%) of [4-amino-3-(dimethoxymethyl)phenyl] phenylmethanone (interm. 64).

b) To a stirred and cooled (10° C.) solution of 22.1 parts of intermediate 64, namely [4-amino-3-(dimethoxymethyl)phenyl] phenylmethanone, in 147 parts of pyridine were added dropwise 12.1 parts of acetyl chloride. After stirring for ½ hour at 10° C. and overnight at room temperature, the reaction mixture was poured into water. The product was extracted with 2,2'-oxybispropane and dichloromethane. The combined extracts were dried, filtered and evaporated. The residue was dissolved in dichloromethane. This solution was washed successively with HCl 0.1N, ammonia and water and was then dried, filtered and evaporated, yielding 27.5 parts (100%) of N-[4-benzoyl-2-(dimethoxymethyl)phenyl]acetamide (interm. 65).

c) To a stirred solution of 25.6 parts of intermediate 65, namely N-[4-benzoyl-2-(dimethoxymethyl)phenyl]acetamide, in 119 parts of methanol were added portionwise 10.72 parts of sodium tetrahydroborate. Stirring was continued for a while at 60° C. and over weekend at room temperature. The reaction mixture was evaporated and the residue was taken up in water. The product was extracted with dichloromethane (2×) and the combined extracts were dried, filtered and evaporated. The residue was purified by column chromatography (silica gel; CH₃COOC₂H₅/hexane 50:50→60:40). The eluent of the desired fraction was evaporated, yielding 13.1 parts (50.8%) of N-[2-(dimethoxymethyl)-4-(hydroxyphenylmethyl)phenyl]acetamide (interm. 66).

d) To a refluxing solution of 13.1 parts of intermediate 66, namely N-[2-(dimethoxymethyl)-4-(hydroxyphenylmethyl)phenyl]acetamide, in 200 parts of dichloromethane was added dropwise a solution of 7.07 parts of 1,1'-carbonylbis[1H-imidazole] in 106.4 parts of dichloromethane. After refluxing for 3½ hours and stirring at room temperature overnight, the reaction mixture was washed with water (2×), dried, filtered and evaporated, yielding 16.6 parts (100%) of N-[2-(dimethoxymethyl)-4-[(1H-imidazol-1-yl)phenylmethyl]phenyl]acetamide (interm. 67).

e) A solution of 2.5 parts of intermediate 67, namely N-[2-(dimethoxymethyl)-4-[(1H-imidazol-1-yl)phenylmethyl]phenyl]acetamide, 52.5 parts of acetic acid and 10 parts of water was stirred for ½ hour at reflux temperature. The reaction mixture was evaporated and the residue was co-evaporated with methylbenzene, yielding 2.2 parts (100%) of N-[2-formyl-4-[(1H-imidazol-1-yl)phenylmethyl]phenyl]acetamide (interm. 68).

EXAMPLE 10

A solution of 13 parts of N-[6-(bromomethyl)-4-hydroxy-2-quinazolinyl]-2,2-dimethylpropanamide, 15.5 parts of 1H-imidazole and 80 parts of acetonitrile was stirred for 4 hours at reflux temperature. The reaction mixture was evaporated and the residue was extracted with ethyl acetate. The extract was washed with NaHCO₃ (aq.), dried, filtered and evaporated. The residue was purified by column chromatography (silica gel; CH₂Cl₂/CH₃OH 98:2). The eluent of the desired fraction was evaporated, yielding 4.3 parts (34.7%) of N-[4-hydroxy-6-(1H-imidazol-1-ylmethyl)-2-quinazolinyl]-2,2-dimethylpropanamide (interm. 69).

B. Preparation of the Final Compounds

EXAMPLE 11

A mixture of 3.6 parts of 6-(chlorophenylmethyl)-3,4-dihydro-2(1H)-quinazolinone, 5.3 parts of 1H-imidazole, 60 parts of acetonitrile and 27.5 parts of dimethyl sulfoxide was stirred for 4 hours at reflux temperature. After concentration, the residue was washed twice with water, dissolved in a mixture of trichloromethane and methanol (90:10 by volume), dried, filtered and evaporated. The residue was purified by column chromatography over silica gel using a mixture of trichloromethane and methanol, saturated with ammonia (95:5 by volume) as eluent. The pure fractions were collected and the eluent was evaporated. The residue was crystallized from a 45 parts of ethyl acetate and a few drops of water. The product was filtered off, washed with ethyl acetate and 2,2'-oxybispropane and dried, yielding 2.3 parts (58.1%) of 3,4-dihydro-6-[(1H-imidazol-1-yl)phenylmethyl]-2(1H)-quinazolinone; mp. 222.5° C. (comp. 16).

EXAMPLE 12

A mixture of 5.8 parts of 6-(chlorophenylmethyl)-2,4(1H,3H)-quinazolinedione, 10 parts of 1H-1,2,4-triazole and 158 parts of acetonitrile was stirred for 1 hour at room temperature and for 2 hours at reflux temperature. The solvent was evaporated and the residue was washed with water. The precipitate was filtered off and purified by column chromatography (silica gel; CH₂Cl₂/CH₃OH 90:10). The eluent of the first fraction was evaporated and the residue was washed with ethyl acetate and dried, yielding 2.2 parts (34.1%)

of 6-[phenyl(1H-1,2,4-triazol-1-yl)methyl]-2,4(1H,3H)-quinazolinedione; mp. 280.9° C. (comp. 40).

EXAMPLE 13

To a stirred and cooled (15° C.) solution of 2.5 parts of 1H-1,2,4-triazole in 70 parts of 1,4-dioxane was added dropwise 1 part of thionyl chloride under nitrogen atmosphere. After stirring for 10 minutes at 20° C., a solution of 2 parts of 6-(cyclopropylhydroxymethyl)-3,4-dihydro-2(1H)-quinazolinone in 80 parts of 1,4-dioxane was added portionwise to the previous mixture at 20°-25° C. After stirring overnight at room temperature, the precipitated product was filtered off, washed with 1,4-dioxane and purified by column chromatography over silica gel using a mixture of dichloromethane, methanol and methanol, saturated with ammonia (90:5:5 by volume) as eluent. The eluent of the desired fraction was evaporated and the residue was further purified, first by column chromatography (HPLC) over silica gel using a mixture of dichloromethane and methanol (96:4 and 97.5:2.5 by volume) and then by column chromatography (RP 18) using a mixture of water and methanol (80:20 by volume) as eluents. The eluent of the desired fraction was evaporated and the residue was stirred in 2,2'-oxybispropane. The product was filtered off, washed with 2,2'-oxybispropane and dried in vacuo at 60° C., yielding 0.04 parts (1.7%) of 6-[cyclopropyl(1H-1,2-4-triazol-1-yl)methyl]-3,4-dihydro-2(1H)-quinazolinone; mp. 184.4° C. (comp. 25).

EXAMPLE 14

A solution of 13 parts of N-[6-(bromomethyl)-4-hydroxy-2-quinazolinyl]-2,2-dimethylpropanamide and 15.5 parts of 1H-imidazole in 80 parts of acetonitrile was stirred for 4 hours at reflux temperature. The reaction mixture was concentrated and the concentrate was extracted with ethyl acetate. The extract was washed with a diluted sodium hydrogen carbonate solution, dried, filtered and evaporated. The residue was purified by column chromatography over silica gel using a mixture of dichloromethane and methanol (98:2 by volume) was eluent. The pure fractions were collected and the eluent was evaporated. A solution of 6.5 parts of the residue in 75 parts of a hydrochloric acid solution 3N was stirred for 2 hours at reflux temperature. The reaction mixture was evaporated to dry and the residue was dissolved in a potassium carbonate solution 40%. The product was extracted with a mixture of dichloromethane and ethanol. The extract was dried, filtered and evaporated. The residue was purified by column chromatography over silica gel using a mixture of dichloromethane, methanol and ammonium hydroxide (90:10:0.1 by volume) as eluent. The pure fractions were collected and the eluent was evaporated. The residue was converted into the hydrochloride salt in ethanol. The salt was filtered off and crystallized from methanol. The product was filtered off and dried, yielding 2.3 parts (23.8%) of 2-amino-6-(1H-imidazol-1-ylmethyl)-4-quinazolinol dihydrochloride; mp. >300° C. (comp. 36).

EXAMPLE 15

To a stirred mixture of 1.7 parts of ethyl [4-[(1H-imidazol-1-yl)phenylmethyl]-2-[(methylimino)methyl]phenyl]carbamate and 31.6 parts of ethanol were added 1 part of sodium tetrahydroborate (portionwise) and 55.3 parts of methanol. After stirring for 7 hours at 40°-50° C., the reaction mixture was evaporated. The residue was taken up in water (to which 0.29 parts of acetic acid were added) and the whole was basified with NH₄OH. The product was extracted with dichloromethane and the extract was dried, filtered and evaporated. The residue was purified by column chromatography (silica gel; CHCl₃/CH₃OH 95:5). The eluent of the desired fraction was evaporated and the residue was crystallized from ethyl acetate, yielding 0.3 parts (20.1%) of 3,4-dihydro-6-[(1H-imidazol-1-yl)phenylmethyl]-3-methyl-2(1H)-quinazolinone; mp. 173.8° C. (comp. 23).

EXAMPLE 16

A solution of 2.2 parts of N-(2-formyl-4-[(1H-imidazol-1-yl)phenylmethyl]phenyl]acetamide and 40 parts of methanol, saturated with ammonia was stirred for 1 hour at room temperature. After evaporation, dichloromethane was added. The solution was filtered and the filtrate was evaporated. The residue was purified by column chromatography over silica gel first using a mixture of dichloromethane and methanol (97:3 by volume) and then a mixture of dichloromethane and methanol (94:6 by volume) as eluents. The eluent of the desired fraction was evaporated and the residue was crystallized from 21 parts of 1,1'-oxybisethane. The product was filtered off and dried, yielding 0.3 parts (14.7%) of 6-[(1H-imidazol-1-yl)phenylmethyl]-2-methylquinazoline; mp. 129.6° C.

EXAMPLE 17

To a stirred solution of 4.6 parts of 2-amino-4-[(1H-imidazol-1-yl)phenylmethyl]benzamide in 90 parts of tetrahydrofuran were added 3.52 parts of 1,1'-carbonylbis[1H-imidazole]. The mixture was stirred first overnight at room temperature and then for 48 hours at reflux temperature. The solution was concentrated under reduced pressure and the concentrate was treated with water. The product was extracted with dichloromethane. A white product was precipitated in the dichloromethane layer. This product was filtered off and crystallized from hot acetonitrile. The product was filtered off, washed with acetonitrile and 2,2'-oxybispropane and dried in vacuo at 60°-70° C., yielding 1.77 parts (35.4%) of 7-[(1H-imidazol-1-yl)phenylmethyl]-2,4(1H,3H)-quinazolinedione; mp. 287.2° C. (comp. 29).

EXAMPLE 18

A mixture of 4.2 parts of 2-amino-4-[(1H-imidazol-1-yl)phenylmethyl]benzamide, 97 parts of trimethoxymethane and 1.3 parts of formic acid was stirred for 5 hours at reflux temperature and overnight at room temperature. The solvent was evaporated and the residue was dissolved in methanol. The solution was basified with ammonious methanol and then evaporated. The residue was purified twice by column chromatography (silica gel; CHCl₃/CH₃OH 95:5; CHCl₃/CH₃OH 90:10). The eluent of the desired fraction was evaporated and the residue was crystallized from acetonitrile. The product was filtered off, washed with 2,2'-oxybispropane and dried, yielding 1 part (23.6%) of 7-[(1H-imidazol-1-yl)phenylmethyl]-4(3H)-quinazolinone; mp. 205.0° C. (comp. 47).

TABLE 6

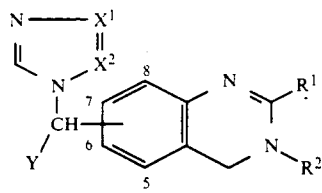

| Comp. No. | Ex. No. | $X^1=X^2$ | Y | p* | $R^1$ | $R^2$ | mp. (°C.)/ base/salt |
|---|---|---|---|---|---|---|---|
| 1 | — | CH=CH | $C_6H_5$— | 6 | H— | $CH_3$— | |
| 2 | — | CH=CH | $C_6H_5$— | 6 | H— | $C_6H_5$—$CH_2$— | |
| 3 | — | CH=CH | $C_6H_5$— | 6 | H— | $C_6H_5$— | |
| 4 | — | CH=CH | $C_6H_5$— | 6 | $CH_3$— | $CH_3$— | |
| 5 | — | CH=CH | $C_6H_5$— | 6 | $CH_3$— | $C_6H_5$—$CH_2$— | |
| 6 | — | CH=CH | $C_6H_5$— | 6 | $CH_3$— | $C_6H_5$— | |
| 7 | — | CH=CH | $C_6H_5$— | 6 | $C_6H_5$— | $CH_3$— | |
| 8 | — | CH=CH | $C_6H_5$— | 6 | $C_6H_5$— | $C_6H_5$—$CH_2$— | |
| 9 | — | CH=CH | $C_6H_5$— | 6 | $C_6H_5$— | $C_6H_5$— | |
| 10 | — | CH=CH | $C_6H_5$— | 6 | $CH_3$— | H— | |
| 11 | — | CH=C($CH_3$) | $C_6H_5$— | 6 | H— | $C_6H_5$—$CH_2$— | |
| 12 | — | C($CH_3$)=CH | $C_6H_5$— | 6 | H— | $C_6H_5$—$CH_2$— | |
| 13 | — | CH=CH | $C_6H_5$— | 6 | $F_3C$— | H— | |
| 14 | — | CH=CH | $C_6H_5$— | 6 | $CH_3O$— | H— | |
| 15 | — | CH=CH | $C_6H_5$— | 6 | Cl— | H— | |

*In the previous and following tables p indicates the position of the 1H-azol-1-ylmethyl moiety on the quinazoline moiety.

TABLE 7

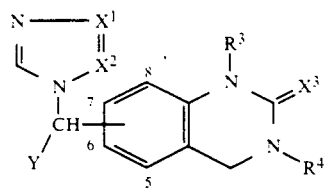

| Comp. No. | Ex. No. | $X^1=X^2$ | Y | p | $R^3$ | $R^4$ | $X^3$ | mp. (°C.)/ base/salt |
|---|---|---|---|---|---|---|---|---|
| 16 | 11 | CH=CH | $C_6H_5$— | 6 | H— | H— | O | 222.5 |
| 17 | 11 | CH=CH | 3-pyridinyl | 6 | H— | H— | O | 240.7 |
| 18 | 11 | CH=CH | i.$C_3H_7$— | 6 | H— | H— | O | >260(dec.)/HCl |
| 19 | 11 | CH=N | $C_6H_5$— | 6 | H— | H— | S | 264.3 |
| 20 | 11 | CH=CH | $C_6H_5$— | 6 | H— | H— | S | 251.7 |
| 21 | 11 | CH=CH | $CH_3$— | 6 | H— | H— | O | 177.0 |
| 22 | 12 | CH=CH | 3-Cl—$C_6H_4$— | 6 | H— | H— | O | 209.3 |
| 23 | 15 | CH=CH | $C_6H_5$— | 6 | H— | $CH_3$— | O | 173.8 |
| 24 | 12 | CH=N | 3-Cl—$C_6H_4$— | 6 | H— | H— | O | 209.2 |
| 25 | 13 | CH=N | c.$C_3H_5$— | 6 | H— | H— | O | 184.4 |
| 26 | — | CH=CH | 3,4$Cl_2$—$C_6H_3$— | 6 | H— | H— | 0 | |
| 27 | — | CH=CH | c.$C_3H_5$— | 6 | H— | H— | 0 | |
| 28 | — | CH=CH | 2-thienyl | 6 | H— | H— | 0 | |
| 29 | — | CH=CH | imidazolyl | 6 | H— | H— | 0 | |
| 30 | — | CH=CH | $CH_3O$—$C_6H_4$— | 6 | H— | H— | 0 | |
| 31 | — | CH=CH | $C_6H_5$— | 6 | $C_6H_5$—$CH_2$— | $C_3H_7$— | 0 | |

TABLE 8

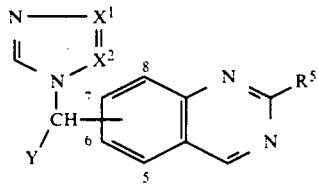

TABLE 8-continued

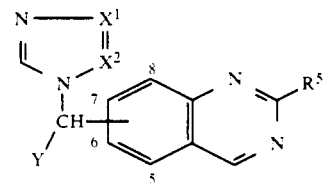

| Comp. No. | Ex. No. | $X^1=X^2$ | Y | p | $R^5$ | mp. (°C.)/ base/salt |
|---|---|---|---|---|---|---|
| 32 | 16 | CH=CH | $C_6H_5$— | 6 | $CH_3$— | 129.6 |
| 33 | — | CH=CH | $C_6H_5$— | 6 | H— | |

TABLE 9

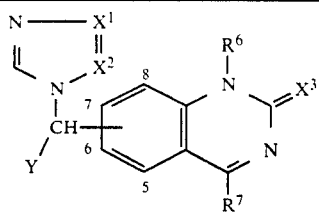

| Comp. No. | Ex. No. | X¹=X² | Y | p | R⁶ | R⁷ | X³ | mp. (°C.)/ base/salt |
|---|---|---|---|---|---|---|---|---|
| 34 | — | CH=CH | $C_6H_5-$ | 6 | H— | $CH_3-$ | O | |

TABLE 10

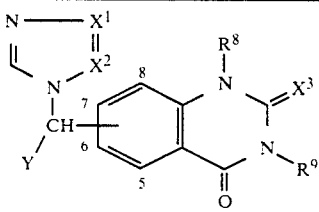

| Comp. No. | Ex. No | X¹=X² | Y | p | R⁸ | R⁹ | X³ | mp. (°C.)/ base/salt |
|---|---|---|---|---|---|---|---|---|
| 35 | 17 | CH=CH | $C_6H_5-$ | 7 | H— | H— | O | 287.2 |
| 36 | 12 | N=CH | $C_6H_5-$ | 6 | H— | $C_6H_5-CH_2-$ | O | 219.8 |
| 37 | 12 | CH=CH | $C_6H_5-$ | 6 | H— | $C_6H_5-CH_2-$ | S | 257.3 |
| 38 | 12 | CH=CH | $C_6H_5-$ | 6 | H— | $C_6H_5-CH_2-$ | O | 263.5 |
| 39 | 12 | CH=N | $C_6H_5-$ | 6 | H— | $C_6H_5-CH_2-$ | O | 204.4 |
| 40 | 12 | CH=N | $C_6H_5-$ | 6 | H— | H— | O | 280.9 |
| 41 | 12 | N=CH | $C_6H_5-$ | 6 | H— | H— | O | 248.0 |
| 42 | 12 | CH=CH | $C_6H_5-$ | 6 | H— | $CH_3-$ | O | >300 (dec.) |
| 43 | 12 | CH=CH | $C_6H_5-$ | 6 | H— | H— | O | >300 (dec.) |
| 44 | — | N=CH | $C_6H_5-$ | 6 | H— | H— | O | |

TABLE 11

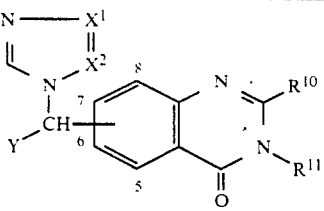

| Comp. No. | Ex. No. | X¹=X² | Y | p | R¹⁰ | R¹¹ | mp. (°C.)/ base/salt |
|---|---|---|---|---|---|---|---|
| 45 | 14 | CH=CH | H— | 6 | $NH_2-$ | H— | >300/ 2HCl |
| 46 | 11 | CH=CH | $C_6H_5-$ | 6 | H— | H— | 208.1 |
| 47 | 18 | CH=CH | $C_6H_5-$ | 7 | H— | H— | 205.0 |

C) Pharmacological Examples

The useful pharmacological properties of the compounds of the present invention can for example be demonstrated by the following experiment.

EXAMPLE 19

Metabolism of Exogenously Administered All-Trans-Retinoic Acid

Male Wistar rats weighing 200~210 g were orally treated with vehicle (PEG 200) or with 40 mg/kg of a compound of formula (I). One hour later, the animals were anesthetized with ether and injected intrajugularly with 0.50 ml saline solution containing 20 μg of all-trans-retinoic acid. Two hours after this injection, rats were killed by decapitation and blood was collected on heparin. Blood samples were centrifuged (1000 g, 15 min) and plasma was recovered to determine the quantity of plasmatic all-trans-retinoic acid. The samples were analyzed by means of HPLC with UV-detection at 350 nm. Quantification was achieved by peak area integration and external standardization. Under the conditions used, plasma concentrations of the retinoic acid in vehicle-pretreated animals were not detectable (<0.5 ng/ml), whereas compound nos. 16, 18, 19, 22, 24, 42 and 46 enhanced the recovery of all-trans-retinoic acid from the plasma to at least 10 ng/ml after dosing with 40 mg/kg.

EXAMPLE 20

Metabolism of Endogenously Administered All-Trans-Retinoic Acid

Male Wistar rats weighing 200~210 g were orally treated with vehicle (PEG 200) or with 40 mg/kg of a compound of formula (I). Two hours after drug administration, the rats were killed by decapitation and blood was collected on heparin. Blood samples were centrifuged (1000 g, 15 min) and plasma was recovered to determine the quantity of plasmatic all-trans-retinoic acid. The samples were analyzed by means of HPLC with UV-detection at 350 nm. Quantification was achieved by peak area integration and external standardization. Under the conditions used, plasma concentrations of the retinoic acid in vehicle-pretreated animals were not detectable (<0.5 ng/ml), whereas compound nos. 18, 19, 20, 24, 38, 42, 43 and 46 enhanced the recovery of all-trans-retinoic acid from the plasma to at least 1 ng/ml.

We claim:

1. A chemical compound having the formula

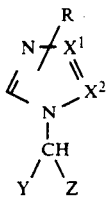

(I)

a pharmaceutical acceptable acid addition salt thereof and the stereochemically isomeric form thereof, wherein —$X^1$=$X^2$— is a bivalent radical having the formula —CH=CH—  (x), —CH=N—  (y), or —N=CH—  (z);

R is hydrogen or $C_{1-6}$alkyl;

Y is hydrogen; $C_{1-10}$alkyl; $C_{3-7}$cycloalkyl; $Ar^1$; $Ar^2$-$C_{1-6}$alkyl; $C_{2-6}$alkenyl or $C_{2-6}$alkynyl;

Z is a radical of formula

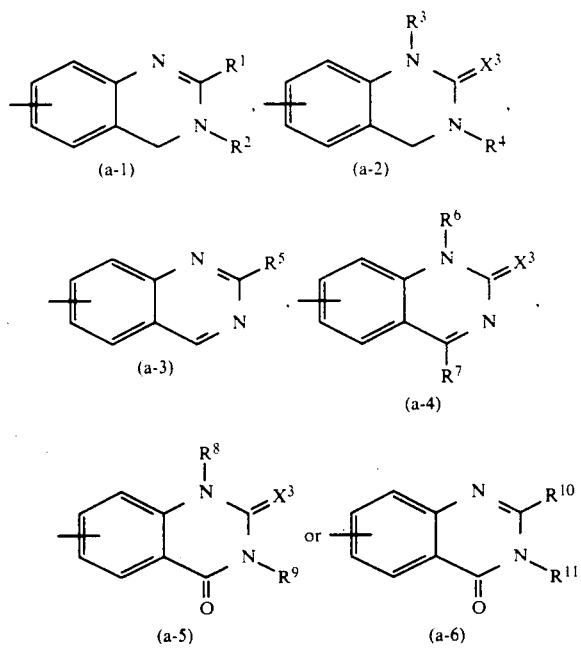

wherein $R^1$, $R^5$ and $R^{10}$ each independently are hydrogen, halo, $C_{1-6}$alkyl, trifluoromethyl, $C_{1-6}$alkyloxy, $Ar^2$, $Ar^2$-$C_{1-6}$alkyl, amino, or mono- or di($C_{1-6}$alkyl)-amino;

$R^2$, $R^4$ and $R^9$ each independently are hydrogen, $C_{1-6}$alkyl, $Ar^2$ or $Ar^2$-$C_{1-6}$alkyl;

$R^3$, $R^6$ and $R^8$ each independently are hydrogen, $C_{1-6}$alkyl or $Ar^2$-$C_{1-6}$alkyl;

$R^7$ is hydrogen or $C_{1-6}$alkyl;

$R^{11}$ is hydrogen, $C_{1-6}$alkyl, $Ar^2$-$C_{1-6}$alkyl, amino or mono($C_{1-6}$alkyl)amino;

$X^3$ is O or S; and $Ar^1$ is phenyl, substituted phenyl, naphthalenyl, pyridinyl, imidazolyl, triazolyl, thienyl, furanyl or thiazolyl and $Ar^2$ is phenyl or substituted phenyl; said substituted phenyl in $Ar^1$ or $Ar^2$ being phenyl substituted with 1, 2 or 3 substituents each independently selected from halo, hydroxy, trifluoromethyl, $C_{1-6}$alkyl, $C_{1-6}$alkyloxy, cyano, amino, mono- and di($C_{1-6}$alkyl)amino, nitro, carboxyl, formyl and $C_{1-6}$alkyloxycarbonyl.

2. A compound according to claim 1 wherein R is hydrogen; Y is hydrogen, $C_{1-6}$alkyl, $C_{3-7}$cycloalkyl, phenyl, substituted phenyl, pyridinyl, imidazolyl or thienyl; Z is a radical of formula (a-1), (a-2), (a-3), (a-4), (a-5), or (a-6) wherein $R^1$ is hydrogen, $C_{1-4}$alkyl, trifluoromethyl or phenyl, $R^2$ is hydrogen, $C_{1-4}$alkyl, phenyl or phenyl-$C_{1-4}$alkyl, $R^3$ is hydrogen or $C_{1-4}$alkyl substituted with phenyl, $R^4$, $R^5$, $R^6$, $R^7$ and $R^8$ are hydrogen or $C_{1-4}$alkyl, $R^9$ is hydrogen, $C_{1-4}$alkyl or phenyl$C_{1-4}$alkyl, $R^{10}$ is hydrogen, amino or mono or di($C_{1-4}$alkylamino), and $R^{11}$ is hydrogen.

3. A compound according to claim 2 wherein —$X^1$=$X^2$— is a radical of formula (x) or (y); R is hydrogen; Y is hydrogen, $C_{1-4}$alkyl, cyclopropyl, cyclohexyl, pyridinyl or phenyl optionally substituted with one or two substituents selected from halo, $C_{1-4}$alkyl, $C_{1-4}$alkyloxy and trifluoromethyl.

4. A compound according to claim 3 wherein Z is a radical of formula (a-2) wherein $R^3$ is hydrogen, $R^4$ is hydrogen or $C_{1-4}$alkyl and Y is hydrogen, $C_{1-4}$alkyl, pyridinyl or phenyl optionally substituted with one or two halo atoms; or Z is a radical of formula (a-3) wherein $R^5$ is $C_{1-4}$alkyl and Y is phenyl or halophenyl; or Z is a radical of formula (a-5) wherein $R^8$ is hydrogen, $R^9$ is hydrogen, $C_{1-4}$alkyl or phenyl$C_{1-4}$alkyl and Y is hydrogen, phenyl or halophenyl; or Z is a radical of formula (a-6) wherein $R^{10}$ is hydrogen or amino, $R^{11}$ is hydrogen and Y is hydrogen, phenyl or halophenyl.

5. A compound according to claim 1 wherein Z is a radical of formula (a-2); —$X^1$=$X^2$— is a radical having the formula (x) or (y); R is hydrogen; $R^3$ is hydrogen; $R^4$ is hydrogen; and Y is phenyl, halophenyl or propyl.

6. A compound according to claim 1 wherein Z is a radical of formula (a-5); —$X^1$=$X^2$— is a radical having the formula (x) or (y); R is hydrogen; $R^8$ is hydrogen; $R^9$ is hydrogen, methyl or $C_{1-4}$alkylphenyl; and Y is phenyl or halophenyl.

7. A compound according to claim 1 wherein Z is a radical of formula (a-6); —$X^1$=$X^2$— is a radical having the formula (x) or (y); R is hydrogen; $R^{10}$ is hydrogen; $R^{11}$ is hydrogen; and Y is phenyl or halophenyl.

8. A compound according to claim 1 wherein the compound is 3,4-dihydro-6-[(1H-imidazol-1-yl)phenylmethyl]-2(1H)-quinazolinone, a pharmaceutically acceptable acid addition salt or a possible stereochemically isomeric form thereof.

9. A compound according to claim 1 wherein the compound is 6-[(1H-imidazol-1-yl)phenylmethyl]-3-methyl-2,4(1H,3H)-quinazolinedione, a pharmaceutically acceptable acid addition salt or a possible stereoisomer thereof.

10. A compound according to claim 1 wherein the compound is 6-[(1H-imidazol-1-yl)phenylmethyl]-

4(3H))-quinazolinone, a pharmaceutically acceptable acid addition salt or a possible stereoisomer thereof.

11. A composition comprising an inert carrier and, if desired, other additives, and as active ingredient an effective amount of a chemical compound claimed in claim 1.

12. A composition according to claim 11 wherein R is hydrogen; Y is hydrogen, $C_{1-6}$alkyl, $C_{3-7}$cycloalkyl, phenyl, substituted phenyl, pyridinyl, imidazolyl or thienyl; Z is a radical of formula (a-1), (a-2), (a-3), (a-4), (a-5), or (a-6) wherein $R^1$ is hydrogen, $C_{1-4}$alkyl, trifluoromethyl or phenyl, $R^2$ is hydrogen, $C_{1-4}$alkyl, phenyl or phenyl$C_{1-4}$alkyl, $R^3$ is hydrogen or $C_{1-4}$alkyl substituted with phenyl, $R^4$, $R^5$, $R^6$, $R^7$ and $R^8$ are hydrogen or $C_{1-4}$alkyl, $R^9$ is hydrogen, $C_{1-4}$alkyl or phenyl$C_{1-4}$alkyl, $R^{10}$ is hydrogen, amino or mono or di($C_{1-4}$alkylamino), and $R^{11}$ is hydrogen.

13. A composition according to claim 12 wherein $-X^1=X^2-$ is a radical of formula (x) or (y); R is hydrogen; and Y is hydrogen, $C_{1-4}$alkyl, cyclopropyl, cyclohexyl, pyridinyl or phenyl optionally substituted with one or two substituents selected from halo, $C_{1-4}$alkyl, $C_{1-4}$alkyloxy and trifluoromethyl.

14. A composition according to claim 13 wherein

Z is a radical of formula (a-2) wherein $R^3$ is hydrogen, $R^4$ is hydrogen or $C_{1-4}$alkyl and Y is hydrogen, $C_{1-4}$alkyl, pyridinyl or phenyl optionally substituted with one or two halo atoms; or Z is a radical of formula (a-3) wherein $R^5$ is $C_{1-4}$alkyl and Y is phenyl or halophenyl; or Z is a radical of formula (a-5) wherein $R^8$ is hydrogen, $R^9$ is hydrogen, $C_{1-4}$alkyl or phenyl$C_{1-4}$alkyl and Y is hydrogen, phenyl or halophenyl; or Z is a radical of formula (a-6) wherein $R^{10}$ is hydrogen or amino, $R^1$ is hydrogen and Y is hydrogen, phenyl or halophenyl.

15. A method of treating mammals suffering from disorders which are characterized by an increased proliferation and/or abnormal differentiation of cells by the systemic or topical administration to said mammals of an effective amount of a chemical compound claimed in claim 1.

16. A method according to claim 15 wherein R is hydrogen; Y is hydrogen, $C_{1-6}$alkyl, $C_{3-7}$cycloalkyl, phenyl, substituted phenyl, pyridinyl, imidazolyl or thienyl; Z is a radical of formula (a-1), (a-2), (a-3), (a-4), (a-5), or (a-6) wherein $R^1$ is hydrogen, $C_{1-4}$alkyl, trifluoromethyl or phenyl, $R^2$ is hydrogen, $C_{1-4}$alkyl, phenyl or phenyl$C_{1-4}$alkyl, $R^3$ is hydrogen or $C_{1-4}$alkyl substituted with phenyl, $R^4$, $R^5$, $R^6$, $R^7$ and $R^8$ are hydrogen or $C_{1-4}$alkyl, $R^9$ is hydrogen, $C_{1-4}$alkyl or phenyl$C_{1-4}$alkyl, $R^{10}$ is hydrogen, amino or mono or di($C_{1-4}$alkylamino), and $R^{11}$ is hydrogen.

17. A method according to claim 16 wherein $-X^1=X^2-$ is a radical of formula (x) or (y); R is hydrogen and Y is hydrogen, $C_{1-4}$alkyl, cyclopropyl, cyclohexyl, pyridinyl or phenyl optionally substituted with one or two substituents selected from halo, $C_{1-4}$alkyl, $C_{1-4}$alkyloxy and trifluoromethyl.

18. A method according to claim 15 wherein

Z is a radical of formula (a-2) wherein $R^3$ is hydrogen, $R^4$ is hydrogen or $C_{1-4}$alkyl and Y is hydrogen, $C_{1-4}$alkyl, pyridinyl or phenyl optionally substituted with one or two halo atoms; or Z is a radical of formula (a-3) wherein $R^5$ is $C_{1-4}$alkyl and Y is phenyl or halophenyl; or Z is a radical of formula (a-5) wherein $R^8$ is hydrogen, $R^9$ is hydrogen, $C_{1-4}$alkyl or phenyl$C_{1-4}$alkyl and Y is hydrogen, phenyl or halophenyl; or Z is a radical of formula (a-6) wherein $R^{10}$ is hydrogen or amino, $R^1$ is hydrogen and Y is hydrogen, phenyl or halophenyl.

19. A method of delaying the metabolism of retinoids in mammals by the systemic or topical administration to said mammals of an amount of a chemical compound claimed in claim 1, effective to delay the degradation of retinoids.

20. A method of treating disorders of keratinization in mammals, said method comprising the topical or systemic administration to said mammals of an amount of a chemical compound claimed in claim 1, effective to inhibit the degradation of retinoids.

* * * * *